United States Patent [19]
Elbein et al.

[11] Patent Number: 5,021,427
[45] Date of Patent: Jun. 4, 1991

[54] NOVEL PYRROLIZIDINE ALKALOID

[75] Inventors: Alan D. Elbein; Joseph E. Tropea, both of San Antonio, Tex.

[73] Assignee: The Board of Regents, The University of Texas System, Austin, Tex.

[21] Appl. No.: 289,907

[22] Filed: Dec. 23, 1988

[51] Int. Cl.[5] .................. C12N 9/99; C12P 17/18; C07D 209/04; C07D 209/52
[52] U.S. Cl. .................. 514/315; 514/412; 435/184; 435/183; 435/119; 435/200; 548/452
[58] Field of Search ............... 435/119, 184, 183, 200; 514/412, 315, 24, 32; 548/452

[56] References Cited

U.S. PATENT DOCUMENTS

| | | | |
|---|---|---|---|
| 4,454,327 | 6/1984 | Butler et al. | 548/452 |
| 4,792,558 | 12/1988 | Sunkara et al. | 514/299 |
| 4,849,430 | 7/1989 | Fleet et al. | 514/315 |

OTHER PUBLICATIONS

Pan et al., *Biochemistry*, vol. 22(16), 1983, pp. 3975-3984.
Sunkara et al., *Biochemical and Biophysical Research Communications*, vol. 148(1), 1987, pp. 206-210.
Walker et al., *Proc. Natl. Acad. Sci.*, vol. 84, 1987, pp. 8120-8124.
Nash et al., *Chemical Abstracts*, vol. 110(11); Mar. 13, 1989; pp. 411-412; #92034e.
Nash et al., *Chemical Abstracts*, vol. 109(13); Sep. 26, 1988; p. 370; #107724k.
Elbein et al., Biochemistry 26, 2502-2510 (1987), "Effect of Isomers of Swainsonine on Glycosidase Activity and Glycoprotein Processing".
Nash, et al., "Isolation from Alexa Leiopetala and X-Ray Crystal Structure of Alexine (1R, 2R, 3R, 7S, 8S)-3-Hydroxymethyl-1,2,7-Trihydroxypyrrolizidine [(2R, 3R, 4R, 5S, 6S)-2-Hydroxymethyl-1-Azabicyclo[3.3.0]Octan-3,4,6-Triol], a Unique Pyrrolizidine Alkaloid" Tetrahedron Lett. 29, 2487-2490 (1988).
CRC Handbook of Chemistry and Physics, 5th Edition, 1964, p. c-15.
Hohenschutz et al., Phytochemistry, vol. 20 (1981) 811-814.
Saul et al., Arch. Biochem. Biophys., vol. 221 (1983) 593-597.
Saul et al., Arch. Biochem. Biophys., vol. 230 (1984) 668-675.
Dreyer, et al., J. Chem. Ecol., vol. 11 (1985) 1045-1051.
Nash, et al., Entomol., vol. 42 (1986) 71-77.
Stevens et al., J. Chem. Ecol., vol. 14 (1988) 1467-1473.
Rhinehart et al., Life Sci., vol. 41 (1987) 2325-2331.
Ostrander et al., Can. Res., vol. 48 (1988) 1091-1094.
Molyneux et al., Science, vol. 216 (1982) 190-191.
Colegate et al., Aust. J. Chem., vol. 32 (1979) 2257-2264.
Humphries et al., Can. Res., vol. 48 (1988) 1410-1415.
Molyneux et al., J. Natural Products, vol. 51 (1988) 1198-1206.

(List continued on next page.)

*Primary Examiner*—Johnnie R. Brown
*Assistant Examiner*—Pamela S. Webber
*Attorney, Agent, or Firm*—Arnold, White & Durkee

[57] ABSTRACT

The present invention involves a purified bioactive compound of the formula:

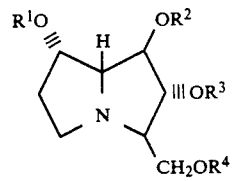

wherein at least one of $R_1$, $R_2$, $R_3$ and $R_4$ are H or an acyl having less than about five carbon atoms. More specifically the preferred purified bioactive compound is (1R, 1R, 3R, 7S, 7aR)-3-hydroxymethyl-1,2,7-trihydroxypyrrolizidine.

9 Claims, 9 Drawing Sheets

AUSTRALINE

OTHER PUBLICATIONS

Molyneux et al., Arch. Biochem. Biophys., vol. 251 (1986) 450–457.

Evans et al., Tetrahedron Lett., vol. 26 (1985) 1465–1468.

Molyneux et al., in Plant Toxicology, Seawright, Hegarty, James and Keller, ed. Queensland Poisonous Plants Comm., Brisbane, Australia (1985) 266–278.

Sawhney et al., Aust. J. Chem., vol. 27 (1974) 1805–1808.

Tropea et al., 17th Annual Meeting of Society for Complex Carbonhydrates, San Antonio, Texas, Nov. 3–5, 1988, Abstract No. 8.

Saul et al., Proc. Natl. Acad. Sci. U.S.A., vol. 82 (1985) 93–97.

Dialog Search Report.

AUSTRALINE

FAGOMINE

ROSMARINECINE

CASTANOSPERMINE

6-EPICASTANOSPERMINE

DMDP

SWAINSONINE

NOVEL PYRROLIZIDINE ALKALOID

Investigations relating to the present invention were supported in part by research grant HL-17783 from the National Institutes of Health (United States Department of Health and Human Services).

BACKGROUND OF THE INVENTION

*Castanospermum australe* A. Cunn. (Leguminosae), the Moreton Bay Chestnut or Black Bean, the monotypic species of the genus Castanospermum native to northeastern Australia, has been introduced into the Indian subcontinent, South Africa and mild climate areas of North America as an ornamental tree. (1) Castanospermine (FIG. 4) the major alkaloidal constituent of the toxic, chestnut-like seeds is a tetrahydroxyindolizidine alkaloid (2) having potent alpha- and beta-glucosidase inhibitory activity (3,4). The consequent modification of glycoprotein processing in cells due to inhibition of glucosidase I (5) ) has stimulated considerable interest in the biological effects of castanospermine on a variety of organisms. The alkaloid is an intensely active feeding deterrent and toxin to certain insects (6,7), and adversely affects root length growth in a number of dicotyledonous plants (8). It has been shown to alter glycogen metabolism and distribution (9) and to block the hyperglycemic response to carbohydrates (10) in rats. In addition, castanospermine inhibits replication of the human immunodeficiency virus (HIV) (11) and other retroviruses (12), and reduces tumor growth in mice (13). Furthermore, the structurally related trihydroxyindolizidine alkaloid swainsonine (FIG. 7), the toxic constituent of locoweeds (14) and Australian Swainsona species (15) is a powerful inhibitor of alpha-mannosidase and exhibits anti-metastatic immunomodulation towards melanoma cells in mice (16). Polyhydroxyindolizidine alkaloids and structurally related analogs may thus represent a class of alkaloids capable of profoundly influencing diverse biological processes due to their glycosidase inhibitory activity (17) and have stimulated efforts to isolate or synthesize additional compounds in order to delineate structure-activity relationships.

Among the common types of glycoproteins that are found in eukaryotic organisms, both as cell-associated proteins and as secreted proteins, are those having N-linked or asparagine-linked oligosaccharides (18; 19). The biosynthesis of the oligo-saccharide portion of these molecules involves a complex sequence of events beginning with the synthesis of the Glc$_3$Man$_9$(GlcNAc)$_2$-pyrophosphoryl-dolichol intermediate and the transfer of the carbohydrate portion of this intermediate to various asparagine residues on the newly-synthesized polypeptide (20, 21, 22). Following the transfer of this oligosaccharide to the protein, the newly formed glycoprotein undergoes a number of modification or "processing" reactions which begin in the endoplasmic reticulum and continue as the glycoprotein is transported through the Golgi to its final destination (23, 24, 25, 26).

The initial processing reactions, catalyzed by two endoplastic reticulum membrane-bound glucosidases, involve the removal of the three glucose residues. Glucosidase I removes the outermost alpha-1, 2-linked glucose residue, while glucosidase II releases the remaining two alpha-1, 3-linked glucoses (27, 28, 29, 30, 31). These trimming reactions give rise to a Man$_9$(GlcNAc)$_2$-protein which may be acted upon by an endoplasmic reticulum-bound alpha-1, 2-mannosidase to give a Man$_8$(GlcNAc)$_2$-oligosaccharide structure (32, 33). The Man$_{8-9}$(GlcNAc)$_2$-protein may be the direct precursor of the high-mannose glycoproteins, or it may be further processed, after translocation to the Golgi, to yield hybrid or complex types of glycoproteins.

In the Golgi, the Man$_{8-9}$(GlcNAc)$_2$-protein may be the substrate for mannosidase I which removes the remaining alpha-1, 2-linked mannose residues, generating a Man$_5$(GlcNAc)$_2$-protein (34, 35, 36, 37, 38). This glycoprotein can then serve as acceptor for GlcNAc transferase I which catalyzes the addition of a GlcNAc, from UDP-GlcNAc, to the mannose that is linked alpha-1, 3 to the beta-linked mannose, resulting in the formation of a GlcNAcMan$_5$(GlcNAc)$_2$-protein (39, 40, 41). Following this addition a second Golgi mannosidase, mannosidase II, catalyzes the removal of the alpha-1, 3 and alpha-1, 6-linked mannose residues generating a GlcNAc-Man$_3$(GlcNAc)$_2$-oligosaccharide (39, 42). Failure to remove these two terminal mannose units can result in the formation of hybrid types of glycoproteins (43, 22). The GlcNAc-Man$_3$(GlcNAc)$_2$-protein can then be the substrate for a series of glycosyltransferases forming the complex types of glycoproteins that contain galactose, sialic acid, fucose, etc. (44, 25).

The study of the biosynthesis of the oligosaccharide portion of the N-linked glycoproteins has been greatly facilitated by the use of inhibitors that act at specific steps in the processing pathway (62, 45). Some of these inhibitors which have gained popularity over the past several years include swainsonine (see FIG. 2), a Golgi mannosidase II inhibitor originally isolated from the Australian plant *Swainsona canescens* (15, 46, 47), deoxymannojirimycin, a synthetic Golgi mannosidase I inhibitor (48, 49, 64), and castanospermine, a glucosidase I/glucosidase II inhibitor isolated from the seeds of the Australian tree *Castanospermum australe* (2, 5, 50).

SUMMARY OF THE INVENTION

The present invention involves a purified bioactive compound of the formula:

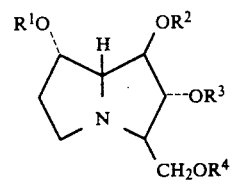

wherein one or more of R$_1$, R$_2$, R$_3$ and R$_4$ are H or acetyl. More specifically the preferred purified bioactive compound is (1R, 2R, 3R, 7S, 7aR)-3-hydroxymethyl-1,2,7-trihydroxypyrrolizidine.

In an important aspect, the present invention involves a method for inhibiting viral or retroviral proliferation in a host. This method comprises administering a therapeutically effective amount of pyrrolizidine alkaloid, preferably tetrahydroxylated, to said host. The therapeutically effective amount should be enough to inhibit said proliferation without causing host toxicity. The preferred pyrrolizidine alkaloid for this method is a purified bioactive compound of the formula:

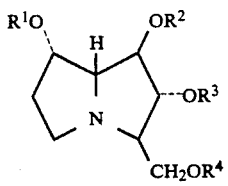

wherein at least one of $R_1$, $R_2$, $R_3$ and $R_4$ is H or an acyl having less than about five carbon atoms. Most preferably the pyrrolizidine alkaloid is (1R, 2R, 3R, 7S, 7aR)-3-hydroxymethyl-1,2,7-trihydroxypyrrolizidine. One retrovirus likely to be so inhibited is HIV-1, the apparent cause of AIDS.

The present invention also involves a method for inhibiting glycosidase activity by use of a pyrrolizidine alkaloid. This method may be practiced in vivo or in vitro. For an in vitro situation, such inhibition comprises incubating glycosidase substrate and glycosidase in the presence of a pyrrolizidine alkaloid, preferably of the formula:

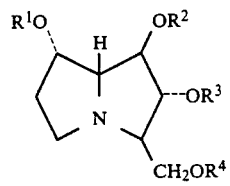

wherein at least one of $R_1$, $R_2$, $R_3$ and $R_4$ is H or an acyl having less than about five carbon atoms. Again, the most preferred pyrrolizidine alkaloid is (1R, 2R, 3R, 7S, 7aR)-3-hydroxymethyl-1,2,7-trihydroxypyrrolizidine. A preferred glycosidase particularly sensitive to such inhibition is alpha glucosidase. A most preferred acyl group is acetyl.

DESCRIPTION OF THE PREFERRED EMBODIMENT

During the purification of castanospermine from the seeds of *C. australe*, the present inventors noted several alkaloid fractions, in addition to the castanospermine fraction, that had inhibitory activity against alpha-glucosidases. By a combination of ion exchange chromatography and preparative centrifugal thin-layer chromatography, a new alkaloid was isolated and named "Australine". The structure of australine (FIG. 1) was established as (1R, 2R, 3R, 7S, 7aR)-3-hydroxymethyl-1,2,7-trihydroxypyrrolizidine. This compound proved to be a good inhibitor of amyloglucosidase and the processing glucosidase I. This is the first demonstration that a pyrrolizidine alkaloid may have glycosidase-inhibitory activity. In addition, Australine inhibited the processing of glycoproteins in cultured cells. Thus, this pyrrolizidine structure represents a new repertoire of chemical structures that can have important inhibitory activity.

EXAMPLE 1

Alkaloid Isolations and Structures

Figure 9:
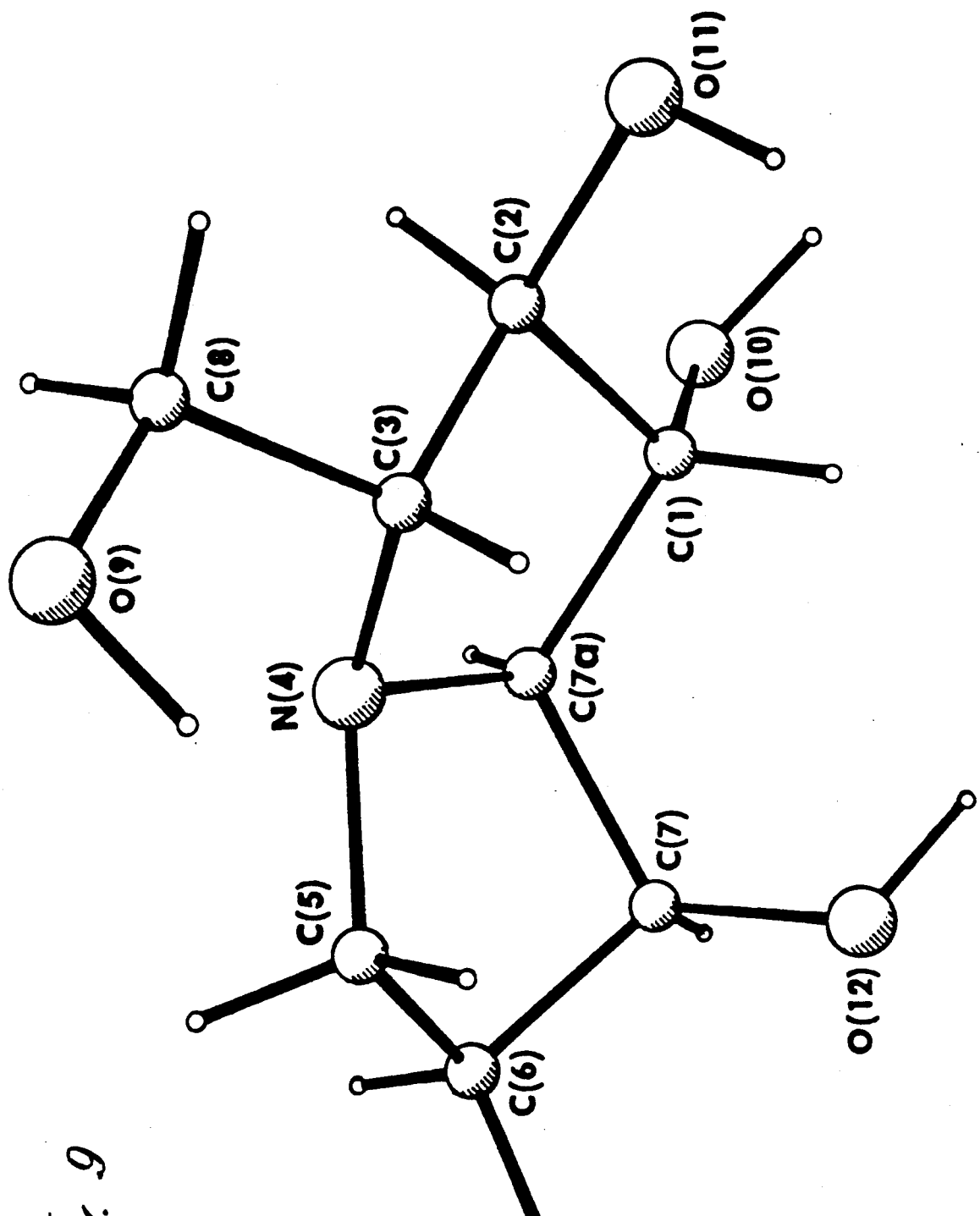
FIG. 9 shows a perspective view of australine with crystallographic numbering scheme. The ascending sizes of shaded circles represent carbon, oxygen and nitrogen atoms respectively.

Thin-layer chromatography of the mother liquors remaining after crystallization of castanospermine (see FIG. 9) from extracts of *C. australe* seeds had indicated the presence of additional alkaloidal constituents.

Figure 5:
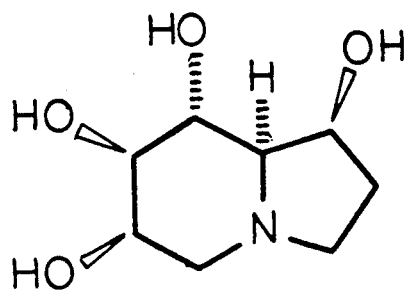
FIG. 5 schematically shows the structure of 6-epicastanospermine.

Separation by preparative centrifugal thin-layer chromatography yielded 6-epicastanospermine (FIG. 5), an inhibitor of alpha-glucosidase (67). In one aspect, the present invention relates to the isolation of fagomine (FIG. 2), a known piperidine alkaloid as well as to the discovery of a potent, specific alpha-glucosidase inhibitor, namely australine. The structure of australine was established by application of one- and two-dimensional high-field nuclear magnetic resonance (NMR) techniques and mass spectrometry (MS) as a tetrahydroxypyrrolizidine alkaloid, and the stereochemistry of the substituents was confirmed by single crystal X-ray crystallography. This is the first report of a pyrrolizidine alkaloid of this type with glycosidase inhibitory properties and represents a novel structural type within the class.

Thin-layer chromatography of the *C. australe* crystallization mother liquors showed a number of components which were less mobile than castanospermine. One of these constituents gave an intense yellow spot with acetic anhydride-Ehrlich's spray reagent and an orange spot with Dragendorff's reagent. Separation by preparative centrifugal thin-layer chromatography gave a crystalline solid, the melting point, optical rotation, $^1$H NMR and MS data of which were consistent with that of fagomine (1,2,5-trideoxy-1,5-imino-D-arabino-hexitol), a piperidine alkaloid first isolated from buckwheat seeds (*Fagopyrum esculentum* Moench) (68). The $^{13}$C NMR of fagomine was measured and assignments confirmed by a two-dimensional heteronuclear $^1$H - $^{13}$C shift correlation experiment. Although fagomine (FIG. 2) has not previously been reported to occur in Leguminosae, the 4-0-(B-D-glucopyranosyl)- derivative has been isolated from seeds of the legume *Xanthocercis zambesiaca* (20). No significant glycosidase inhibitory activity was found when fagomine was tested against commercially available alpha-and beta-glucosidase, galactosidase and mannosidase, in accord with previous results (69).

Australine (FIG. 1) was isolated by repeated preparative centrifugal thin-layer chromatography as a colorless oil which was crystallized from acetone with some difficulty as small, dextrorotatory prisms, m.p. 148°-149°. The moleoular formula was determined by high-resolution mass spectrometry to be $C_8H_{15}NO_4$. The alkaloid formed a tetraacetate derivative under mild acetylation conditions indicating the presence of four primary or secondary hydroxyl groups. However, on thin layer chromatography this alkaloid gave a weak blue-gray spot with acetic anhydride-Ehrlich's spray reagent rather than the intense purple spot characteristic of polyhydroxyindolizidine alkaloids. The latter color is produced by dehydration and rearrangement to give a pyrrole ring system which undergoes condensation with the 4-dimethylaminobenzaldehyde at the position alpha- to the nitrogen atom (70). The pyrrole ring generated from australine must therefore bear a substituent blocking the alpha-position. Moreover, the electron impact mass spectrometry (EIMS) showed no ion corresponding to the six-membered ring fragment, resulting from cleavage of bonds B to the nitrogen atom in the pyrrolidine ring moiety (17), typical for castanospermine and other indolizidine alkaloids. Instead, the base peak occurred at m/z 158[M-31]$^+$, indicating loss of an exocyclic —CH$_2$OH group. The fundamental ring system was thus shown to be of the pyrrolizidine type. Other major fragments observed in the mass spectrum were typical for this class of compound, resulting from cleavage of either of the five-membered rings at bonds B to the nitrogen atom. The masses of these ions were such that a single —OH group had to reside on one ring while the remaining two —OH groups and the —CH$_2$OH moiety fully substituted the alternate ring. In all saturated necine bases previously isolated, such as rosmarinecine (FIG. 3) which bear the —CH$_2$OH group at the 1-position, the major mass spectral fragments result from cleavage of the ring system. In contrast, the major fragment from australine is a consequence of the loss of —CH$_2$OH, indicating that this substituent must be B to the nitrogen atom at the 3-position.

Figure 4:
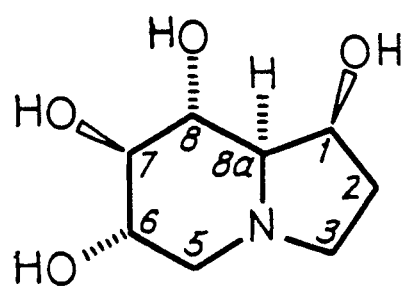
FIG. 4 schematically shows the structure of castanospermine.
Figure 6:
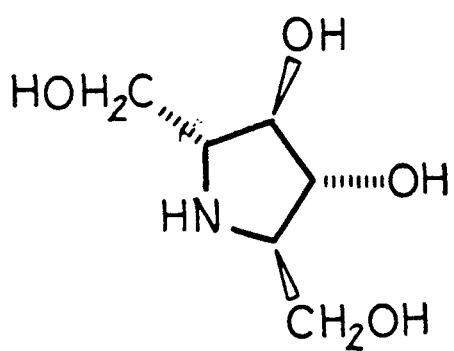
FIG. 6 schematically shows the structure of DMDP (dihydroxymethyl-dihydroxypyrrolizidine).

Conclusive evidence regarding the presence of a pyrrolizidine ring system and the position of substituents was obtained from the $^{13}$C and $^1$H NMR spectra determined in $D_2O$. Whereas the $^{13}$C spectrum of australine showed the presence of five methine and three methylene signals, as in castanospermine (FIG. 4) and 6-epicastanospermine (FIG. 5), distinct chemical shift differences were immediately apparent. Thus, although two of the methylene signals (delta-38.1 and delta-54.9) corresponded closely to those in the five-membered ring of the latter alkaloids, the third signal at delta-65.6 occurred significantly downfield from those observed for methylene groups at the 5-position of castanospermine (delta-54.3) and 6-epicastanospermine (delta-54.6). However, its value corresponded well with that observed for the symmetrically disposed —CH$_2$OH groups (delta-63.9) in dihydroxymethyldihydroxypyrrolidine (FIG. 6) (DMDP) measured under identical conditions and thus confirmed the occurrence of such a substituent in australine.

Figure 7:
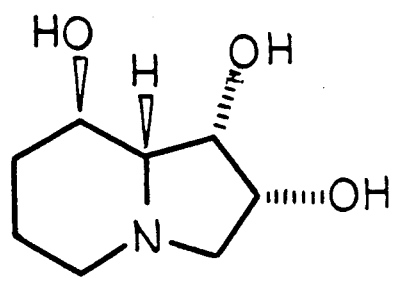
FIG. 7 schematically shows the structure of swainsonine.

The high-resolution $^1$H NMR spectrum also demonstrated notable variations in chemical shifts of the well-separated groups of signals in comparison to those of the tetrahydroxyindolizidine alkaloids. In particular, while castanospermine and its 6-epimer show only a single signal below delta-4.0, corresponding to the proton at the hydroxylated 1-position, australine shows two signals at delta-4.58 and delta-4.41 together with a third at delta-3.92. In this respect it is comparable to swainsonine (FIG. 7) which has —OH groups located at the 1- and 1-positions of the five-membered ring and exhibits two signals at delta-4.43 and delta-4.33 respectively with a third at delta-3.88, all of which are due to protons on hydroxylated positions B to the nitrogen atom. In the high-field region from delta-1.5–2.5, australine showed only a two-proton multiplet centered at delta-2.03, whereas castanospermine has five signals corresponding to the H-3B, H-5B and bridgehead H-8a protons, which are essentially trans-diaxial to the nitrogen lone-pair (71), together with both H-2 protons. However, the existence of only a single signal at lower field (delta-3.18) and two overlapping signals at delta-2.93 and 3.03 in australine indicated that the latter must be due to the H$_{5alpha}$ and H$_{3alpha}$ protons, which are trans-diaxial to the nitrogen lone pair. The differences in the $^1$H spectra, which are much more apparent than those noted in the $^{13}$C spectra, confirm the fundamental distinction between castanospermine and australine, namely the cis-fusion of the bicyclic ring system required for a pyrrolizidine alkaloid (71), rather than the energetically favored trans-fusion of the indolizidine alkaloids.

Figure 1:
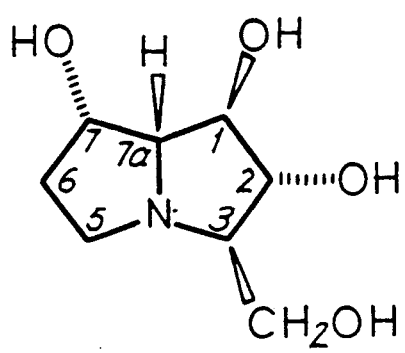
FIG. 1 schematically describes the structure of australine (1R, 2R, 3R, 7S, 7aR)-3-hydroxymethyl-1,2,7-trihydroxypyrrolizidine.
Figure 8:
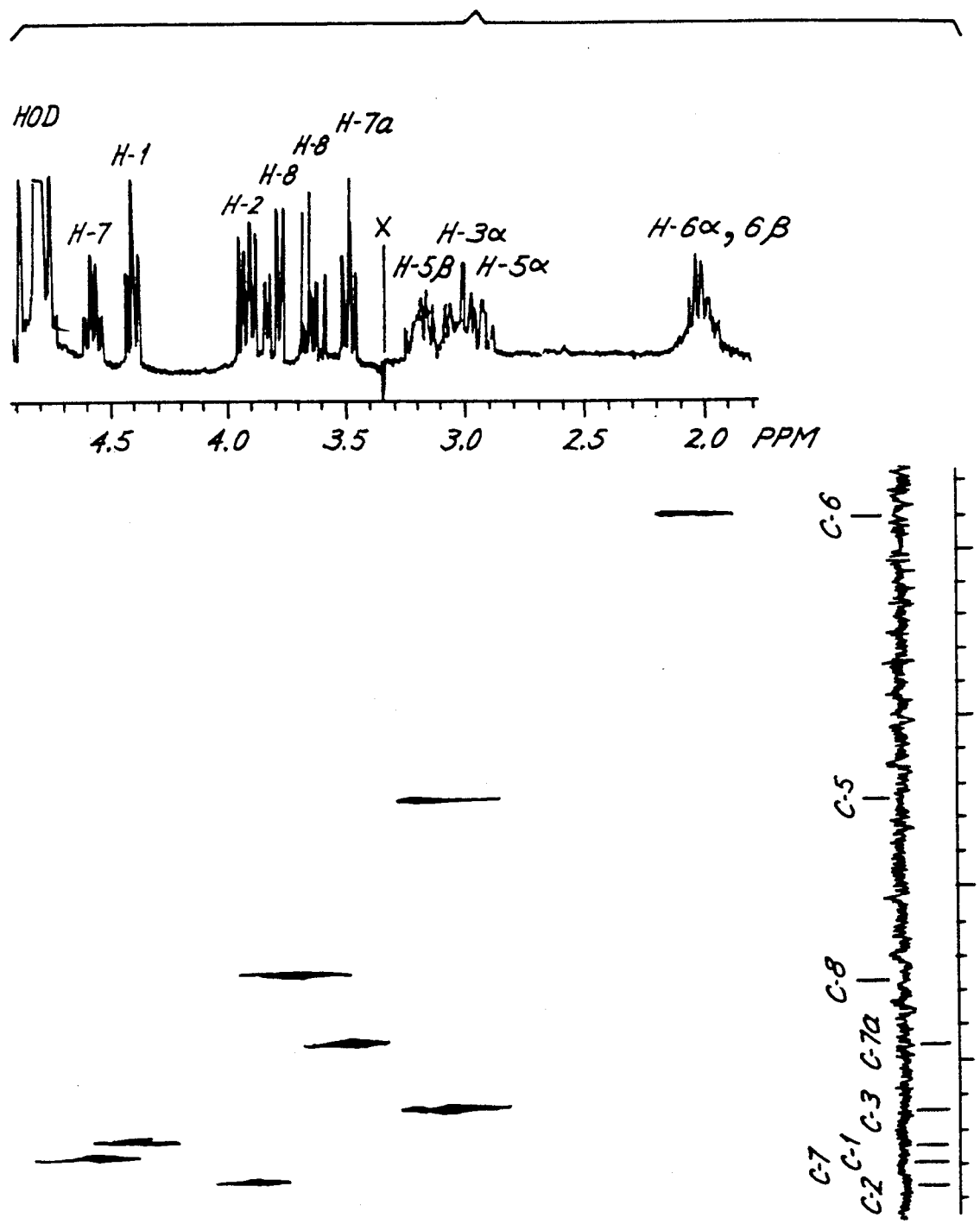
FIG. 8 shows the two-dimensional $^1H$-$^{13}C$ NMR shift correlation spectrum of australine [1] in $D_2O$.

Extensive decoupling experiments established the connectivity and substitution pattern of australine as shown in FIG. 1 and yielded the requisite coupling constants. Of particular significance was irradiation of the lowest field signal at delta-4.58 which resulted in collapse of the high-field multiplet at delta-2.03, which must correspond to H-6-alpha and H-6-beta, and also the double doublet at delta-3.46, thus identifying the latter signal as the bridgehead 7a-H. This resonance also collapsed upon irradiation of the low-field signal at delta-4.41, which must be due to H-1, since the only other signal affected was the quartet at delta-3.92 (H-2). Irradiation of the multiplet at delta-3.03 (H-3) influenced not only the H-2 quartet but also the well-separated-CH$_2$OH proton signals at delta-3.64 and delta3.81. The non-equivalence of these protons must be attributable either to restricted rotation (71) or to intramolecular hydrogen-bonding of the hydroxyl group to the nitrogen lone-pair. A two-dimensional heteronuclear $^1$H - $^{13}$C shift correlation experiment was used to confirm assignments of the $^{13}$C NMR chemical shifts, the results of which are shown in FIG. 8. The signal for the —CH$_2$OH group occurred at delta-65.6 and the bridgehead C-7a at delta-68.9, as predicted from appropriate models (14). The four remaining methine carbon atoms, which are bound either to an oxygen or nitrogen atom, resonated in the narrow range of delta-72.9–77.3.

Figure 3:
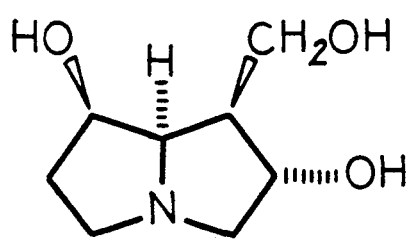
FIG. 3 schematically shows the structure of rosmarecine.

Determination of the coupling constants from the above experiments established the identical value of 5 Hz for $J_{1,7a}$, $J_{1,2}$ and $J_{7,7a}$ and a value of 9 Hz for $J_{2,3}$. The latter coupling constant is consistent with trans protons which exist in a near-diaxial situation (theta ~ 160°) such as occur in croalbinecine (72) and rosmarinecine (FIG. 3). In australine therefore the 2-OH and the —CH$_2$OH groups must have a trans disposition to one another. In this event the magnetic non-equivalence of the —CH$_2$OH protons is unlikely to be due to restricted rotation. The 5 Hz coupling constants are unfortunately intermediate in magnitude between those reported for cis protons and for protons having a trans relationship in the above examples, and also in swainsonine (FIG. 7) and its di- and tri-acetate derivatives (15). Values observed for protons in a cis relationship (theta is about 30°) are generally in the range of 3–4 Hz, whereas those for trans protons are 8–10 Hz. Although the coupling constants of 5 Hz in australine are somewhat closer to those expected for cis substitution, chemical evidence argued against such a relationship, at least for the —OH groups in the 1- and 1- positions. Thus, treatment of the alkaloid with 2,2-dimethoxypropane in the presence of p-toluenesulfonic acid failed to give an acetal derivative. Moreover, from examination of molecular models, the stereoisomer in which the —OH groups at the 1- and 7-positions bear a cisoid relationship to one another and are in close proximity, might also have been expected to yield a six-membered ring acetal derivative. These results are therefore consistent with a structure for australine in which the 1-OH group is trans to those at the 2- and 7-positions.

In view of the uncertainty of the stereochemical structure of australine based upon the NMR data, due to the known sensitivity of J values to slight variations in theta in five-membered ring systems, together with the potential for exo- or endo-flipping in saturated pyrrolizidine alkaloids (71), the stereochemistry was ascertained by an alternate method. Crystals sufficiently large for X-ray crystallographic analysis were obtained, with some difficulty, by slow crystallization from acetone and the structure, stereochemistry and absolute configuration of australine thereby established as (1R, 2R, 3R, 7S, 7aR)-3-hydroxymethyl-1,2,7-trihydroxypyrrolizidine. The molecular conformation is illustrated as a perspective drawing in FIG. 9. The crystal structure consists of two crystallographically independent molecules within each asymmetric unit. Except for minor differences in the values of analogous bond lengths and bond angles, both molecules possess similar structural features. The two five-membered rings are symmetrically endo-buckled with C-2 and C-6 being 09.6-alpha above the mean plane of the other four atoms of their respective rings. The endo-buckling presumably reduces non-bonded interaction between H-3-alpha and H-5-alpha and between H-1 and the —OH group at the 7-position (71). The molecule is folded along the nitrogen-bridgehead carbon bond, resulting in a dihedral angle between the two ring planes of approximately 54°. the three hydroxyl groups have a transoid configuration and the orientation of the —CH$_2$OH substituent is noteworthy. It assumes a position with the hydroxyl group directed towards the nitrogen lone pair, enhancing the formation of an intramolecular hydrogen bond (O(9) . . . N(4)=3.1-alpha) and concomitant five-membered chelate ring, thus accounting for the non-equivalence of the —CH$_2$OH protons in the NMR spectrum.

The molecules in the crystal structure mutually interact with adjacent molecules through an intricate arrangement of intermolecular hydrogen bonds formed by the nitrogen and oxygen atoms of adjacent unit molecules. The short intermolecular contacts between oxygen-oxygen and oxygen-nitrogen atoms are within the range of 2.68–2.89-alpha. The unusual feature of the crystal structure, comprising two crystallographically independent molecules per assymetric unit, is possibly due to the tendency of these molecules to form a considerable number of relatively strong hydrogen bonds between each other, enhancing a more compact and stable molecular packing in the crystal.

The trihydroxypyrrolizidine alkaloid rosmarinecine (FIG. 3) had been tested earlier and found to lack glycosidase inhibitory activity. However, australine proved to be a potent and specific inhibitor of amyloglucosidase (an exo-1,4-alpha-glucosidase ($K_i$=5.2 micro M) whereas castanospermine inhibited both alphaglucosidase ($K_i$- 7.9 micro M) and beta-glucosidase. No significant inhibition of beta-glucosidase, alpha- and beta-mannosidase or alpha- and beta-galactosidase was observed.

Australine is therefore not only the first tetrahydroxypyrrolizidine alkaloid to be isolated but also possesses a unique substitution pattern, bearing the hydroxymethyl group at the 3-position rather than the previously invariant 1-position. In addition it is the sole member of its class to be shown to be a glycosidase inhibitor. Previously identified classes of glycosidase inhibitors have been limited to the polyhydroxy-indolizidines (e.g. castanospermine), - pyrrolidines (e.g. DMDP) and -piperidines (e.g. nojirimycin). The structure of australine (FIG. 1) is presented in the conventional manner for all pyrrolizidine alkaloids, namely with the most highly substituted ring on the right. Its relationship to castanospermine (FIG. 4) can be visualized by inverting the molecule from right to left.

GENERAL EXPERIMENTAL PROCEDURES. The alkaloids were monitored for purity by tlc on 0.25 mm silica gel plates developed with $CHCl_3$:MeOH:$H_4OH$:$H_2O$ (70:26:2:2) and detected by spraying with acetic anhydride followed by Ehrlich's reagent (21). Homogeneity was also checked by gc of the TMS derivatives, prepared by treatment with MSTFA in pyridine, on a Hewlett-Packard 5830 instrument equipped with a flame-ionization detector, on-column injector, and a 30-m×0.32-mm i.d. SE-30 fused silica column. Low resolution electron and ammonia chemical ionization mass spectra were obtained on a VG Micromass 7070 mass spectrometer; high resolution mass measurements were determined on the same instrument. Optical rotations were measured in a 1-dm cell on a Perkin-Elmer 241 automatic polarimeter. Nuclear magnetic resonance spectra were determined in $D_2O$ on a Nicolet NTC 200FT spectrometer with software package at 200 MHz ($^1H$) and at 50.3 MHz ($^{13}C$) using 3-(trimethylsilyl)-1-propanesulfonic acid (TSP) as an internal standard. Multiplicities for $^{13}C$ signals were determined by application of the carbon attached proton test (CAPT) sequence. Preparative centrifugal tlc was performed on a Chromatotron Model 7924 (Harrison Research, Palo Alto, Calif.). Enzyme assay methods have been previously described (67), Melting points are uncorrected.

PLANT MATERIAL. Seeds of *C. australe* were collected from the Huntington Botanical Gardens, San Marino, Calif.

EXTRACTION AND FRACTIONATION. Mature seeds were ground and extracted with MeOH in a Soxhlet apparatus and the alkaloidal fraction purified by ion-exchange chromatography on Dowex 50W-H8 ($NH_4^+$ form) (2). The eluate was repeatedly subjected to crystallization from MeOH until no additional castanospermine, m.p. 217°-219°, could be isolated. Portions of crystallization mother liquors (200 mg.) were fractionated by preparative centrifugal tlc on a 2 mm. silica gel plate by sequential elution with $CHCl_3$:MeOH:$NH_4OH$:$H_2O$ (70:26:2:2) (120 ml.) and EtOH:$NH_4OH$ (98:2) (200 ml.). A total of 70 fractions (ca. 4.5 ml each) were collected. Fractions showing similar tlc profiles were pooled and concentrated. Residual castanospermine eluted in fractions 21-32 (70 mg.).

Figure 2:
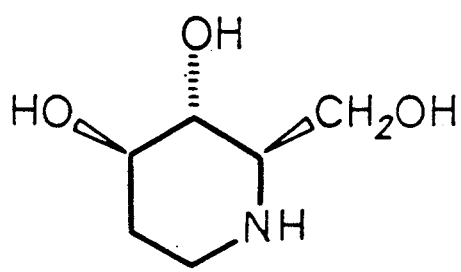
FIG. 2 schematically shows the structure of fagomine.

ISOLATION AND CHARACTERIZATION OF FAGOMINE FIG. 2). Combined fractions 31-44 (22 mg.) gave a discrete, bright yellow spot on tlc ($R_F$=0.12) which was slightly less mobile than castanospermine ($R_F$ - 0.14). GC analysis of the TMS derivative gave a single peak with a retention time ($R_T$) of 12.07 mins. Castanospermine has $R_T$ 19.22 mins. The colorless oil slowly crystallized and was recrystallized from MeOH-EtOH as white cubes, m.p. 184°-185°, lit. m.p. for fagomine, 186°-188° (68). The $^1H$ NMR and mass spectra were completely in accord with data previously reported for fagomine (68); $^{13}C$ NMR (50.3 MHz, $D_2O$) delta-75.9 (C-3), 75.8 (C-4), 64.2 (C-6), 63.6 (C-5), 45.3 (C-1), 35.3 (C-2); optical rotation [alpha-]$^{24}$. $_{lambda}$ (c 0.51, MeOH): +24.4° (589),+25.5° (578)+28.9° (546),+48.5 (436),+73.9° (365), lit. [alpha-]$^{20}$delta=24.7° (c 0.4, $H_2O$) (69). Fagomine showed no inhibitory activity when tested against a number of generally available glycosidases, as previously reported (69).

ISOLATION AND CHARACTERIZATION OF AUSTRALINE (FIG. 1). Evaporation of combined fractions 45-65 gave a clear, colorless oil (61 mg.) which showed a blue-gray spot on tlc ($R_F$=0.08). GC of the TMS derivative gave a single peak with $R_T$ 17.07 min. Crystallization from $Me_2CO$ afforded australine as colorless prisms, mp 148°-149°; [alpha-]$^{26}$$_{lambda}$(c 2.09, MeOH):+19.3° (589),+19.9° (578), +22.1° (546),+32.8° (436),+42.3° (365); $^1H$ NMR (200 MHz $D_2O$) delta-4.58 (1H, q, $J_{6-alpha,7}$+9 Hz, $J_{7,7alpha}$+5 Hz, H-7), 4.41 (1H, dd, $J_{1,2}$=$J_{1,7}$-alpha=5 Hz, H-1, 3.92 (1H, dd, $J_{1,2}$=5 Hz, $J_{2,3}$=9 Hz, H-2), 3.812 (1H, dd, $J_{3,8}$=4 Hz, $J_{gem}$= -12 Hz, H-8), 3.64 (1H, dd, $J_{3,8}$=6.5 Hz, $J_{gem}$= -12 Hz, H-8), 3.46 (1H, dd, $J_{1,7alpha}$=$J_{7,7alpha}$=5 Hz, H-7alpha), 3.18 (1H, m, H-5beta), 3.03 (1H, m, H-3alpha), 2.93 (1H, m, H-5alpha), 2.02 (2H, m, H-2-alpha, 2beta); $^{13}C$NMR (50.3 MHz, $D_2O$) delta-77.3 (C-2), 75.8 (C-7), 74.9 (C-1), 72.9 (C-3), 68.9 (C-7alpha), 65.6 (C-8), 54.9 (C-5), 38.1 (C-6; $^1H$ - $^{13}C$ 2-D shift correlation NMR ($D_2O$): see FIG. 9; EIMS m/z [M]$^+$ 189(5), 159(16), [M-$CH_2OH$] 158(100), 129(10), 128(14), 114(11), 112(43), 98(8), 86(38), 70(22); EIMS ($NH_3$) m/z [MN]$^+$ 190(100), [MH-$H_2O$[$^+$ 172(6), 158(40); hrms, mass measurement [M]$^+$ m/z 189.0998 (calcd for $C_8H_{15}NO_4$, 189.1001).

PREPARATION OF AUSTRALINE TETRAACETATE. Australine (10 mg) in dry pyridine (0.3 ml) was treated with $Ac_2$ (0.5 ml) and kept at room temperature for 20 hours. The clear solution was poured into $H_2O$ (20 ml), the aqueous mixture extracted with $CHCl_3$ (3×10 ml) and the organic layer dried over anhydrose $MgSO_4$, filtered and evaporated to give a colorless oil (15 mg); $^1H$ NMR (200 MHz, $CDCl_3$) delta-5.47 (1H, dd), 5.27 (2H, m), 4.17 (1H, dd), 4.04 (1H, dd), 3.54 (1H, q), 3.22 (1H, m), 3.13 (1H, m), 3.13 (1H, m), 2.71 (1H, m), 2.15-2.00 (2H, m), 2.13 (3H, s, —OAc), 2.09 (3H, s, —OAc), 2.08 (3H, s, —OAc), 2.04 (3H, s, —OAc); $z^{13}$ NMR (50.3 MHz, $CDCl_3$) delta-170.7 (—$OCOCH_3$), 170.5 (—$OCOCH_3$), 170.0 (—$OCOCH_3$), 169.8 (—$OCOCH_3$), 77.9 (C-6), 73.8 (C-1), 73.4 (C-7), 69.5 (C-5), 66.8 (C-7alpha), 64.4 (C-8), 52.1 (C-3), 33.9 (C-2), 21.1 (—$OCOCH_3$), 20.84 (2x —O-

COCH$_3$), 20.76(—OCOCH$_3$); EIMS m/z [M]+ 357(0.8), [M - OAc]+ 314(1.3), 29 (22), [M - CH$_2$OAc]+ 28(40), 237(9), 182(21), 178(100), 164(54), 122(50), 43(98); EIMS (NH$_3$), m/z [MH]+ 358(100), 316(3), 297(3), 284(3), 240(4), 236(8), 178(16), 164(6), 136(6), 118(7); hrms, mass measurement [m]+ m/z 357.1431 (calcd. for C$_{16}$H$_{23}$NO$_8$, 357.1423).

It is understood that those skilled in the art of synthetic organic chemistry could readily use numerous other carboxylic acid anhydrides or chlorides to esterify one or more of the hydroxyl groups of australine. Acyl functions having less than about five carbon atoms could be easily synthesized and be likely to have analogous biological activity.

X-RAY STRUCTURE DETERMINATION. A single crystal of australine, monoclinic space group, P2$_1$, a=8.132(2), b=9.337(2), c=21.219(3)alpha, beta=106.61(2)° was used. Intensity data was collected on a Nicolet R3 diffractometer with graphite monochromatized Cu-K$_{alpha}$ radiation (lambda=1.5418alpha) by the theta -2 theta scan technique at room temperature. The crystal structure was solved by direct methods. The final least squares structure refinement converged at R=0.050 and R (weighted)=0.063. The absolute configuration was determined by comparison of R-values for the two enantiomeric structures.

Australine, a tetrahydroxy pyrrolizidine alkaloid with a unique substitution pattern, has been isolated from seeds of *Castanospermum australe* and shown to be a potent and specific inhibitor of amyloglucosidase. The structure was established by a combination of spectroscopic and chemical techniques and confirmed by X-ray crystallography. Australine is the first pyrrolizidine alkaloid to be identified as a glycosidase inhibitor and is the third glucosidase inhibitor, together with the indolizidine alkaloids castanospermine and 6-epicastanospermine isolated from *C. australe*. In addition to these bicyclic alkaloids, the piperidine alkaloid fagomine, a non-inhibitor, has been isolated from these seeds.

EXAMPLE 2

Alkaloid biological activity

Abbreviations used herein include:
Con A, Concanavalin A
Endo H, endo-beta-N-acetylglucosaminidase H
MDCK cells, Madin-Darby canine kidney cells
MES, 2-(N-morpholino)ethanesulfonic acid
PBS, phosphate buffered saline
TCA, trichloroacetic acid
TFA, trifluoroacetic acid
Tris, tris(hydroxymethyl)aminomethane Materials. [2-$^3$H] Mannose (15 Ci/mmole) and [6-$^3$H]galactose (15 Ci/mmole) were purchased from American Radiolabeled Chemicals, Inc. [4,5-$^3$H]Leucine (50 Ci/mmole) was obtained from ICN, pronase was from Calbiochem, and endo-beta-N-acetylglucosaminidase H (Endo H[1]) was from Miles Scientific. Concanavalin A-Sepharose 4B, maltitol, amyloglucosidase (from *Aspergillus niger*), beta-glucosidase (from almonds), alpha-galactosidase (from *Aspergillus niger*), beta-galactosidase (from bovine liver), alpha-mannosidase (from jack bean), and all p-nitrophenyl-glycoside substrates were purchased from Sigma Chemical Company. Beta-Mannosidase was purified from *Aspergillus niger* as previously described (51). Glucosidase I and glucosidase II were partially purified from mung bean seedlings (50). [$^3$H]Glucose-labeled Glc$_3$Man$_9$GlcNAc-oligosaccharide was isolated from influenza virus-infected MDCK cells labeled with [6-$^3$H]galactose in the presence of castanospermine (52). Tissue culture materials were obtained from Flow Laboratories. Bio-Gel P-4 and Bio-Gel P-2 were purchased from Bio-Rad Laboratories, and Sephadex LH-20 was purchased from Pharmacia Fine Chemicals. Australine was isolated from *Castanospermum australe* mother liquors by ion exchange chromatography and TLC (53). Castanospermine was isolated from *Castanospermum australe* mother liquors by crystallization as reported elsewhere (2, 54). All additional chemicals were analytical grade.

Enzyme Assays. (A) glycosidases. The enzymatic activities of amyloglucosidase, beta-glucosidase, alpha- and beta-galactosidase, and alpha- and beta-mannosidase were determined colorimetrically by monitoring the release of p-nitrophenol from the appropriate p-nitrophenylglycoside substrate (55). All reaction mixtures contained 20 micromoles sodium acetate buffer, pH 5, 2 micromoles of nitrophenyl-glycoside, and enzyme in a final volume of 0.4 ml. Incubations were at 37° C. for 15 min, and the reactions were stopped by the addition of 2.5 ml of 0.4 M glycine, pH 10.4. The p-nitrophenol liberated in the reaction was measured at 410 nm using a Gilford spectrophotometer. Assays were done under conditions where the amount of p-nitrophenol released was linear with both time and protein concentration. For inhibition studies, australine (or castanospermine) was preincubated with enzyme (20 min) prior to the addition of substrate. For competition analyses, australine and substrate were added simultaneously.

(B) Sucrase and Maltase. Intestinal sucrase and maltase activities were determined by measuring the formation of reducing sugar from sucrose and maltitol, respectively. The reaction mixture contained 7.5 micromoles sodium citrate buffer, pH 6, 9 micromoles of substrate (sucrose or maltitol), and enzyme, in a final volume of 0.3 ml. The mixtures were incubated at 37° C. for 10 min, and the formation of reducing sugar was determined by the Nelson method (56). For both enzymes, activity was proportional with time, and amount of protein. As described above for the arylglycosidases, inhibitors were preincubated with enzyme prior to the addition of substrate.

(C) Glucosidase I and Glucosidase II. Glucosidase I activity was determined by measuring the release of [$^3$H]glucose from [$^3$H]glucose-labeled Glc$_3$Man$_9$GlcNAc as described previously (52). Glucosidase II activity was measured by monitoring the release of p-nitrophenol from p-nitrophenyl-alpha-D-glucoside (55). The incubation mixtures for both enzymes contained 50 nM MES buffer, pH 6.5, 0.1% Triton X-100, enzyme, and substrate (25,000 cpm of Glc$_3$Man$_9$GlcNAc for glucosidase I; 1.25 micromoles p-nitrophenyl-alpha-D-glucoside for glucosidase II), in a final volume of 0.25 ml. A typical incubation was for 1 hour at 37° C., and was linear with both time and protein concentration for the duration of the assay.

Growth and Labeling of Influenza Virus. The NWS strain of influenza virus was grown in MDCK cells as previously described (5, 57). MDCK cells were maintained in 75 cm$^2$ tissue culture flasks in modified Eagle's medium containing 10% fetal bovine serum. At confluency, the cells were infected with influenza virus at a multiplicity of infection of approximately 75PFU. One hour after infection, australine was added to a final concentration of 10–500 micro g/ml. Following an incubation period of 2 hours to allow the alkaloid to take effect, [6-$^3$H]galactose or[2-$^3$H]mannose was added to each culture (both at 25 micro Ci/ml) and the cells were allowed to incubate for an additional 48 hours to form mature virus. The presence of mature virus was determined by hemagglutination. When the titer reached a maximum, the medium, containing viral particles and cell debris, was removed and saved, and any cells still adhered to the flasks were removed with a rubber policeman and pooled with the medium. The pooled fraction was subjected to low speed centrifugation to remove cell debris, and the supernatant was then centrifuged at 100,000×g for 18 hours to pellet the virus.

Preparation and Analysis of Glycopeptides. The mature influenza virus, isolated by ultracentrifugation, was exhaustively digested with Pronase to obtain a glycopeptide fraction for analysis. Briefly, viral pellets were suspended in 2 ml of 50 mM Tris buffer, pH 7.5, containing 1 mM $CaCl_2$. An equal volume of a 5 mg/ml Pronase solution (in the same buffer) was added, and the mixtures were incubated at 37° C. for 18 hours under a toluene atmosphere. The Pronase treatment was repeated a second time. The reaction mixture was then treated with TCA to a final concentration of 5%. After a 30 min incubation in an ice-water bath, precipitated protein was removed by centrifugation, and the supernatant liquid was extracted repeatedly with ethyl ether to remove any remaining TCA. The neutralized solution, containing glycopeptides, was then concentrated to a small volume for analysis by gel filtration.

Glycopeptides were separated on a 1.5×100 cm column of Bio-Gel P-4 (100–200 mesh) equilibrated in 1% acetic acid. Aliquots of column fractions were analyzed for radioactivity to identify the positions of the glycopeptide and free sugar(s) peaks. Since this column did not completely resolve the complex-types of glycopeptides from the high-mannose types, the entire glycopeptide peak was pooled and digested exhaustively with Endo H. For these incubations the entire glycopeptide peak was concentrated to dryness and then suspended in 2 ml of 50 mM citrate buffer, pH 6. Ten milli units of Endo H (in the same buffer) was added, and the mixtures were incubated at 37° C. for 18 hours under a toluene atmosphere. At the end of this time, a second addition of Endo H was made (10 m units) and the incubation was repeated. These digests were then rechromatographed on the same Bio-Gel P-4 column and the Endo H-sensitive peaks were identified by a shift of the radiolabeled glycopeptide peak to the right (i.e., eluting later from the column).

Characterization of Oligosaccharides. The structure of the Endo H-sensitive oligosaccharide(s) produced in the presence of australine was determined by a combination of chromatographic, enzymatic and chemical methods. Prior to analysis, each oligosaccharide fraction was subjected to affinity chromatography on Con A-Sepharose 4B to remove any contaminating complex type structures. One ml columns of Con A-Sepharose 4B were equilibrated with 50 mM Tris buffer, pH 7.5, containing 150 mM NaCl, 1 mM $CaCl_2$, 1 mM $MgCl_2$, and 1 mM $MnCl_2$. The sample was applied to the column, and the column was washed with 20 ml of the equilibration buffer. Bound oligosaccharide was eluted from the column with 100 mM alpha-methylmannoside in the above buffer, and the free alpha-methylmannoside was removed from the oligosaccharide peak by desalting on a BioGel P-2 column. The oligosaccharide eluting in the void peak of the Bio-Gel P-2 column was used for structural analysis.

(A) Chromatographic Methods. Endo H-susceptible, Con A-purified oligosaccharide was chromatographed on a calibrated 1×200 cm column of Bio-Gel P-4 (200–400 mesh), equilibrated in 1% acetic acid. The size of the oligosaccharide was determined after radioactive counting of the column eluant and comparison to migration of standard oligosaccharides.

(B) Enzymatic Methods. [$^3$H]Glucose-labeled oligosaccharides were treated with partially purified glucosidase I and glucosidase II to determine their enzymatic susceptibilities. Digestions were performed as described for the Enzyme Assays (see above), and were analyzed by monitoring the release of free glucose and determining the size of the oligosaccharide product.

(C) Methylation Analysis. [$^3$H]Glucose-labeled oligosaccharides produced in the presence of australine were subjected to exhaustive methylation by a modification (58) of the method described by Hakomori (59). Lyophilized oligosaccharide was dissolved in 2 ml of dimethylsulfoxide under nitrogen, and combined with 1 ml of dimethylsulfoxide containing 100 mg methylsulfinyl carbanion. The mixture was sonicated for 5 hours at 40°–50° C., then chilled on ice to 4° C. Two ml of $CH_3I$ were added and the sample was sonicated for 2 hours at 4° C. with the addition of another 2 ml of $CH_3I$ after 1 hour. After standing at room temperature overnight, the mixture was passed through a column of Sephadex LH-50 equilibrated with 80% methanol (4° C.), in order to remove dimethylsulfoxide, methylsulfinyl carbanion and other salts. The column eluates, corresponding to methylated oligosaccharides, were pooled, concentrated to dryness, and hydrolyzed in 2 N TFA at 110° C. for 4 hours under vacuum. Methylated sugars were then analyzed by thin-layer chromatography on 0.5 mm Kiesel Gel 60 F-254 plates (Merck) developed with benzene:acetone:water:ammonium hydroxide (50:200:3:1.5). Standard methylated glucose derivatives prepared from maltose, kojibiose, nigerose, and isomaltose were run in parallel lanes. Methylated standards were visualized by charring the plates after spraying with 5% ethanolic $H_2SO_4$. Radioactive methylated sugars were detected by scraping the plates into 0.5 cm sections followed by liquid scintillation counting.

Synthesis of Lipid-linked Saccharides and Protein. The effect of australine on the formation of lipid-linked saccharides and on protein synthesis was tested in uninfected MDCK cells. Confluent monolayers of MDCK cells, in 6-well Linbro tissue culture dishes, were treated for 2 hours with various concentrations of australine (50–500 micro g/ml) in modified Eagle's medium containing 10% fetal bovine serum. The cells then were incubated for 15–120 min with either [2-$^3$H]mannose (20 micro Ci/ml) or [4,5-$^3$H]leucine (10 micro Ci/ml) to label lipid-linked saccharides and cellular proteins, respectively. At the end of the labeling period, the medium was removed by aspiration, and the monolayers were washed 3 times with PB S. One ml of PBS was added to each well, the cells were dislodged by scraping, and were then quantitatively transferred to reaction tubes. Each well was washed with another 1 ml of PBS and this rinse was also added to the initial tube. Radioactivity incorporated into lipid-linked monosaccharides and oligosaccharides was determined after extraction with chloroform:methanol:water (1:1:1) and chloroform:methanol:water (10:10:3), respectively, as previously described (60). For the incorporation of radiolabel into protein, cells were extracted with TCA at a final concentration of 20% in the presence of 500 micro g of bovine serum albumin. Following an overnight incubation at 4° C., precipitated protein was isolated by centrifugation. The precipitate was washed twice with 5% TCA, and once with absolute methanol, and then digested with Pronase as described above. Pronase-released radioactivity was measured by liquid scintillation counting.

Figure 10:
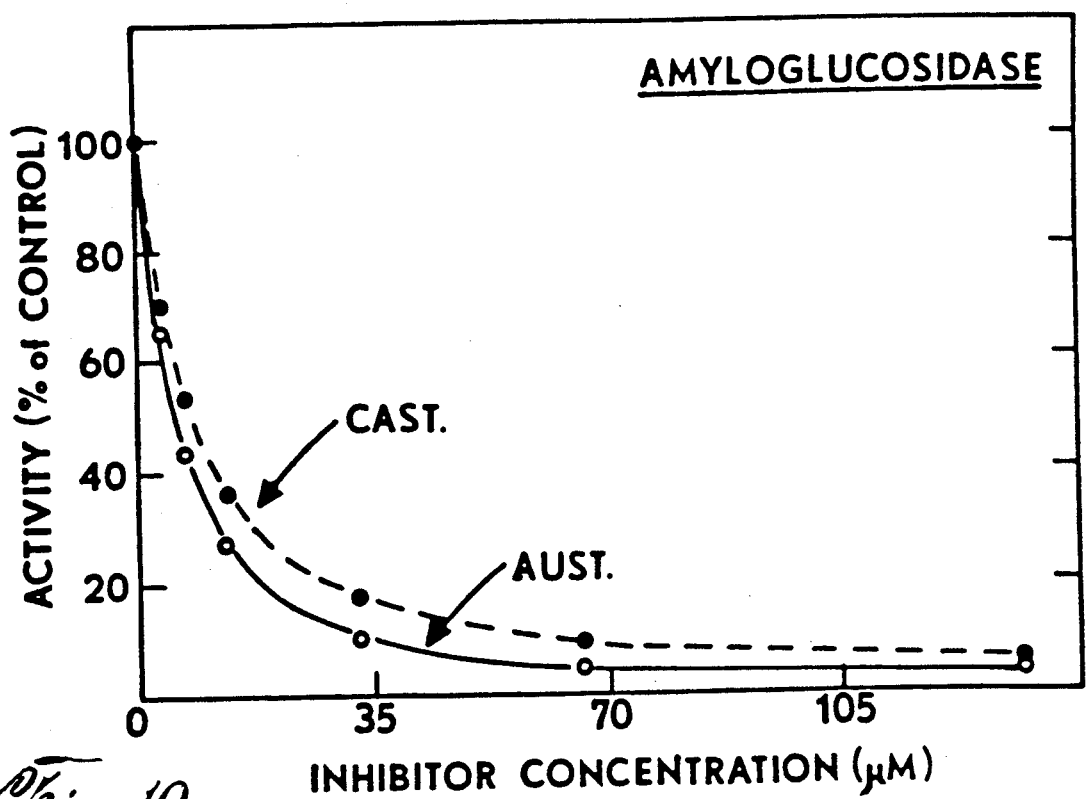
FIG. 10 shows the pattern of amyloglucosidase inhibition by australine and castanospermine. Incubations were as described herein using p-nitrophenyl-alpha-D-glucoside as substrate. Activity was expressed relative to untreated enzyme. Australine (AUST), . Castanospermine (CAST), .
Figure 11:
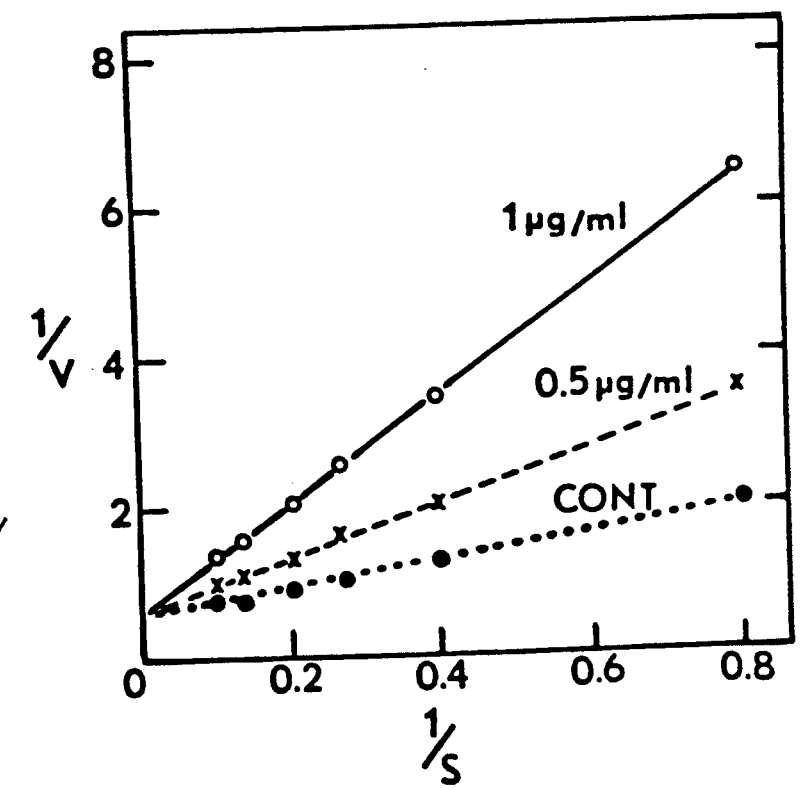
FIG. 11 shows the effect of substrate concentration on australine inhibition of amyloglucosidase. Incubations were as described herein except that various amounts of p-nitrophenyl-alpha-D-glucoside were added with inhibitor (0.5 micro g/ml australine, ; 1 micro g/ml australine, , or without inhibitor (control, CONT), as indicated. The data were plotted according to the method of Lineweaver and Burk.

Effect of Australine on Various Glycosidases. Australine was tested against a number of commercially available glycosidases to determine inhibitory activity. Like castanospermine, australine was found to be a potent inhibitor of amyloglucosidase, an alpha-1 → 4, alpha-1 → 6 exoglucosidase (FIG. 10), with an apparent Ki of 5.8 micro M. The type of inhibition was competitive in nature (FIG. 11) indicating a structural similarity to the substrate, similar to that found for castanospermine (4). In contrast to castanospermine, however, australine was found to be a poor inhibitor of beta-glucosidase. For example, at levels of castanospermine which inhibited 50% of the beta-glucosidase activity (66 micro M), australine inhibited less than 5%.

In addition to alpha- and beta-glucosidase, australine was also tested against alpha- and beta-mannosidase and alpha- and beta-galactosidase for inhibitory activity. At concentrations up to 500 micro M, australine had no apparent effect on any of these hydrolases.

Figure 12:
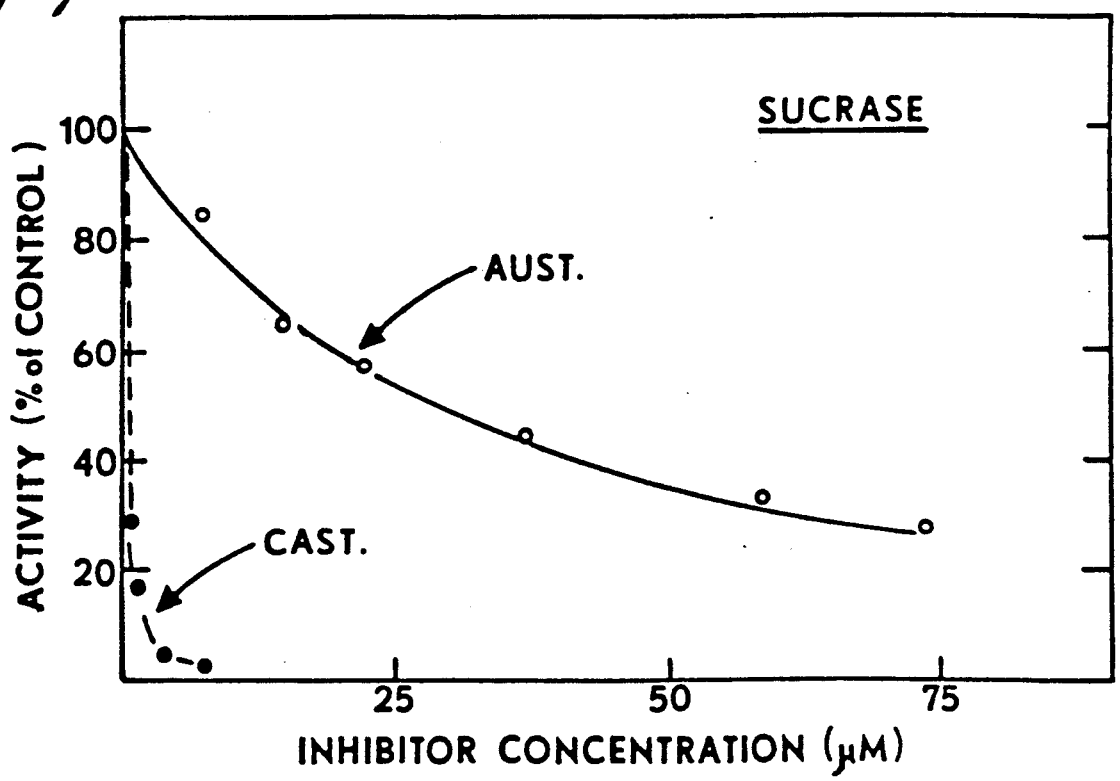
FIG. 12 shows a comparison of the effect of australine and castanospermine on intestinal sucrase activity. Incubations were as described herein using sucrose as substrate. Activity is expressed relative to untreated enzyme. Australine (AUST), . Castanospermine (CAST), .
Figure 13:
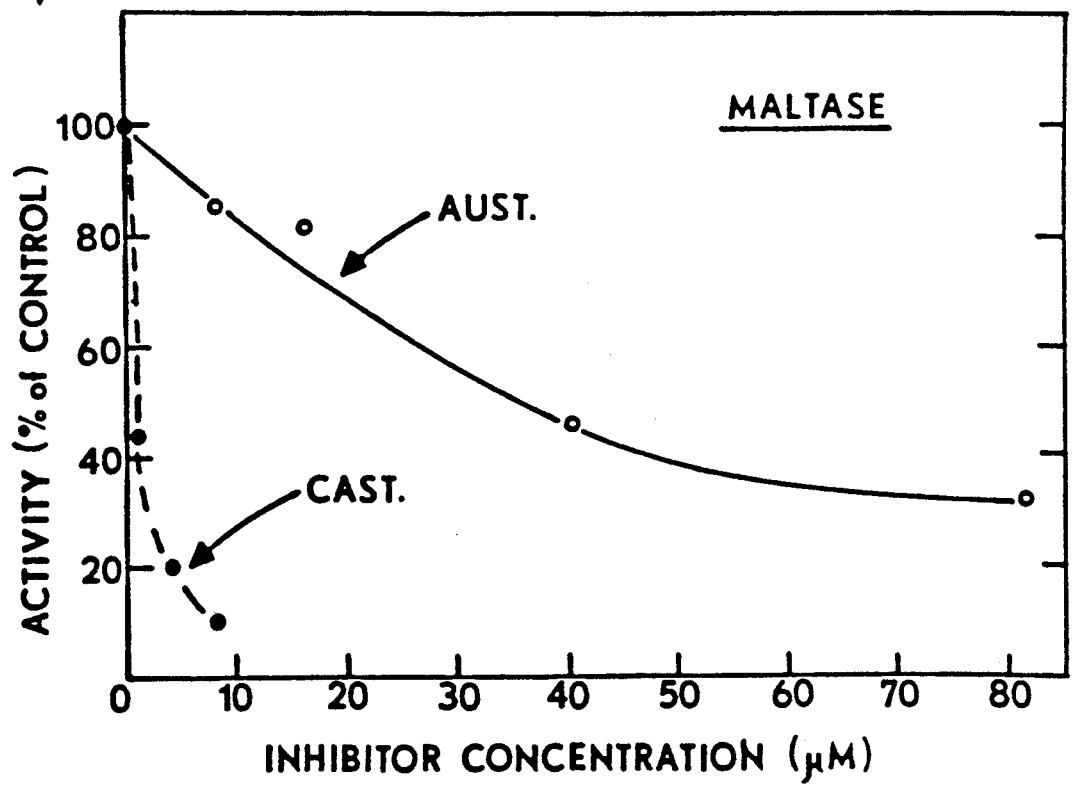
FIG. 13 shows a comparison of the effect of australine and castanospermine on intestinal maltase activity. Incubations were as described herein using maltitol as substrate. Activity is expressed relative to untreated enzyme. Australine (AUST), . Castanospermine (CAST), .

Effect of Australine on Sucrase and Maltase. The effects of australine toward other enzymes that are sensitive to castanospermine, namely intestinal sucrase and maltase (61), were also measured. The results of these studies are shown in FIGS. 12 and 13 for sucrase and maltase, respectively. Although australine did show significant levels of inhibition within the micromolar range for both enzymes (Ki of approximately 28 micro M for sucrase and 35 micro M for maltase), relative to castanospermine the inhibition was poor (Ki for both enzymes less than 1 micro M).

Effect of Australine on Processing Glucosidases. Australine was also tested for inhibitory activity against partially purified glucosidase I and glucosidase II from mung bean seedlings. These hydrolases, which are inhibited by micromolar amounts of castanospermine (see FIG. 14), are involved in the initial oligosaccharide-trimming reactions in the endoplasmic reticulum during N-linked glycoprotein processing. The results shown in FIG. 14 demonstrate quite clearly that australine selectively inhibits glucosidase I (FIG. 14, lower panel), having no activity against glucosidase II (FIG. 14, upper panel) even at concentrations up to 500 micro M. Although the inhibitory activity toward glucosidase I is less potent relative to castanospermine (Ki of approximately 20 micro M for australine vs. Ki of approximately 1 micro M for castanospermine), australine is the first example of a compound inhibiting glucosidase I without also inhibiting glucosidase II.

Figure 15:
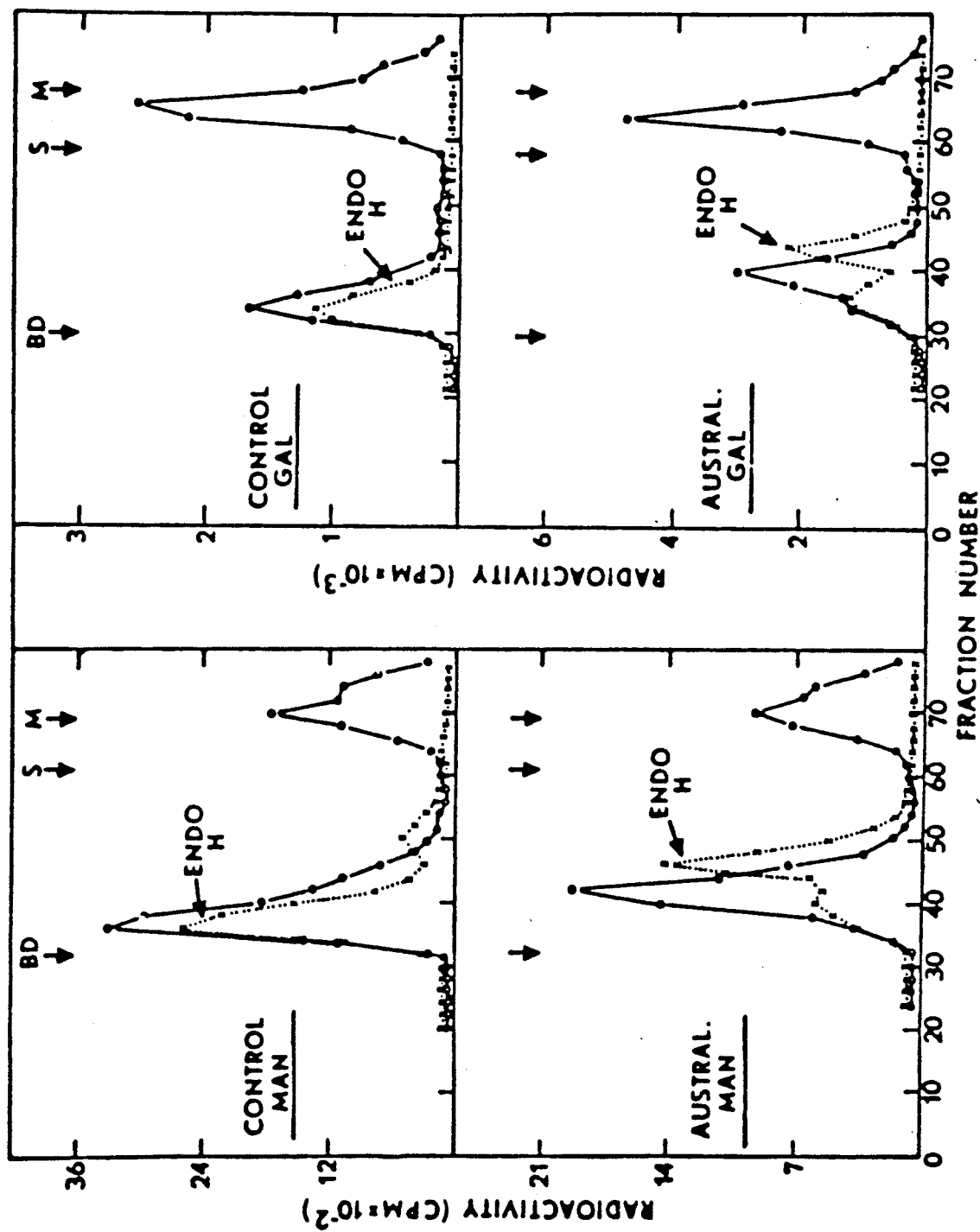
FIG. 15 shows the effect of australine on the oligosaccharide composition of influenza virus glycoproteins. Infected MDCK cells were incubated for 2 hours with 500 micro g/ml australine (lower profiles), and then labeled with either [$^3H$] mannose (MAN, left) or [$^3H$] galactose (GAL, right). Control flasks (upper profiles) were done in the absence of alkaloid. After an incubation of 48 hours, the virus particles were isolated from treated and untreated cultures by ultracentrifugation and digested exhaustively with Pronase as described herein. The glycopeptides were separated on columns of Bio-Gel P-4 (1.5×100 cm) (0—0). The entire glycopeptide peak (fractions 32–52 for mannose-labeled material or fractions 30–48 for glucose-labeled material) was pooled, digested with Endo H, and rechromatographed on the same Bio-Gel column(X    X). Radioactivity was determined by liquid scintilation counting. The arrows indicate the positions of calibration markers: BD, blue dextran T-2000; S, stachyose; M, mannose.

Effect of Australine on Glycoprotein Processing in Culture. Australine was tested to determine whether it would alter normal glycoprotein processing in cell culture. For these studies, influenza virus-infected MDCK cells were incubated for 2 hours in the absence or presence of various concentrations of australine, and then the cultures were labeled for 48 hours with either [2-$^3$H]mannose or [6-$^3$H]galactose. The mature virus was isolated by differential centrifugation and digested exhaustively with pronase to generate glycopeptides. The glycopeptides were then isolated by chromatography on columns of Bio-Gel P-4. FIG. 15 shows representative radioactive profiles of those glycopeptides from virus raised in the absence (upper panels) or presence (lower panels) of 500 micro g/ml of australine (0—0). since these columns did not give good resolution of the complex from the high-mannose structures, the entire glycopeptide peak was pooled for each sample, digested with Endo H, and re-chromatographed on the same Bio-Gel P-4 (FIG. 15; X—X).

It can be seen from the upper profiles of FIG. 15 that the glycopeptides from control virus, labeled with either [$^3$H]mannose or [$^3$H]galactose, emerged from the column as a single asymmetrical peak. Exhaustive digestion with Endo H of the glucose-labeled glycopeptide peak produced no change in the radioactive profile relative to the undigested material (fractions 30–42), while treatment of the mannose-labeled glycopeptide peak (fractions 32–46) with Endo H produced a smaller second peak (fractions 46–58) containing approximately 18% of the total incorporated radioactivity. The bulk of the radioactivity of the Endo H-treated mannose-labeled glycopeptide, however, remained in a position identical to that of the untreated glycopeptide peak, and like the glucose-labeled material, represents glycopeptide with complex oligosaccharide structures. The smaller second peak most likely represents oligosaccharide of the high-mannose type and is consistent with the observation that influenza viral hemagglutinin contains about 20–30% high-mannose oligosaccharide side-chains (5).

When virus was raised in the presence of 500 micro g/ml australine, a much different glycopeptide profile was observed after Bio-Gel P-4 chromatography (FIG. 15, lower profiles). For both mannose-labeled and glucose-labeled material, there was a shift of the glycopeptide peaks, with the bulk of the bound radioactivity eluting from the Bio-Gel P-4 columns at later positions relative to their controls. Furthermore, when these glycopeptide peaks were treated with Endo H there was a massive release of labeled oligosaccharide comprising 71% of the bound radio-activity in the mannose-labeled glycopeptide, and 65% of the bound radio-activity in the glucose-labeled oligosaccharide. These results indicate that australine altered the normal processing of the viral glycoproteins generating a greatly-increased proportion of high-mannose, Endo H-sensitive oligosaccharides. Moreover, the observation that the Endo H-released oligosaccharide from the glucose-labeled glycopeptides contained bound radioactivity suggested that australine blocked glucose removal, most likely by an inhibition of glucosidase I.

In addition to the studies shown in FIG. 15, australine was also tested in virus-infected MDCK cell cultures at several intermediate concentrations, and was found to affect glycoprotein processing in a dose-dependent manner. Thus, at a final concentration of 10 micro g/ml this proportion increased to 55%. Comparable values for glucose-labeled glycopeptide were 17% and 38% release of bound oligosaccharide at a final concentration of 10 micro g/ml and 50 micro g/ml of australine, respectively.

Australine was tested as an inhibitor of the replication of the human immunodeficiency virus (HIV-1) in tissue culture cells. Australine inhibited the growth of the virus, but this alkaloid was not as effective as an inhibitor as was castanospermine, another alkaloid produced by this same plant. On the other hand, since australine is more specific towards the alpha-glucosidases than is castanospermine, it should be less toxic that castanospermine. It could thus be a better therapeutic agent even if a high dose is required. In addition, since australine is a pyrrolizidine alkaloid (whereas castanospermine is an indolizidine alkaloid), it may be more easily chemically synthesized.

Figure 16:
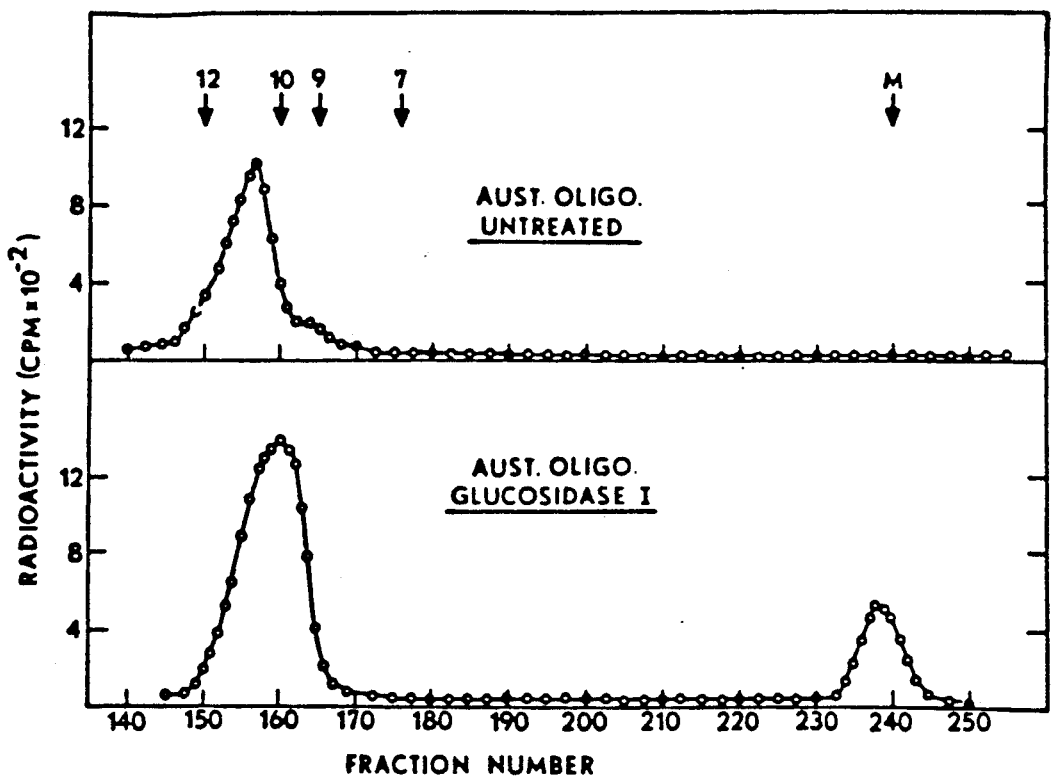
FIG. 16 shows a partial characterization of the glucose-labeled oligosaccharide produced in the presence of australine. The Endo H-released oligosaccharide (see FIG. 15) from virus grown in the presence of 500 micro g/ml australine (AUST. OLIGO.) was chromatographed on a 1 ×200 cm column of Bio-Gel P-4 (200–400 mesh). Radioactivity in various fractions was determined by liquid scintillation counting. The upper panel shows the molecular sizing of the untreated Endo H-sensitive oligosaccharide while the lower panel shows the effect of glucosidase I treatment prior to chromatography. Standard oligosaccharides (arrows) are $Glc_3Man_9GlcNAc$ (12), $Glc_1Man_9GlcNAc$ (10), $Man_9GlcNAc$ (9), and $Man_7GlcNAc$ (7). M, mannose.

Characterization of the Oligosaccharide Produced in the Presence of Australine. The glucose-labeled, Endo H-released, oligosaccharide produced in the presence of 500 micro g/ml of australine was isolated from the Bio-Gel P-4 column shown in FIG. 15. After Con A-Sepharose 4B purification (as described above), the oligosaccharide was applied to a long calibrated column of Bio-Gel P-4 to obtain an accurate size determination. FIG. 16 (upper panel) shows that the majority of the radioactivity eluted from this column in the position expected for a hexose$_{11}$GlcNAc structure and was clearly distinct from the hexose$_{12}$-GlcNAc and hexose$_{10}$GlcNAc standards. This observation was consistent with a Glc$_3$Mn$_8$GlcNAc oligosaccharide structure. Further evidence in support of this was obtained by enzymatic treatment of the Endo H-released oligosaccharide with glucosidase I (FIG. 16, lower panel). Since this enzyme will only act on structures containing a terminal alpha-1,2-linked glucose unit, the appearance of free glucose after incubation is strong proof for the presence of a Glc$_3$-oligosaccharide structure. The results of FIG. 16 (lower panel) demonstrate quite clearly that after incubation of the glucose-labeled oligosaccharide with glucosidase I (free of glucosidase II), there was a release of free glucose concomitant with a change in the size of the resulting oligosaccharide to a hexose$_{10}$GlcNAc structure, consistent with the loss of a single glucose unit. In addition to these observations, incubation of the Endo H-released hexose$_{11}$GlcNAc with partially purified glucosidase II (free of glucosidase I) resulted in the release of only small amounts of radioactive glucose, suggesting that most of the australine-induced oligosaccharide contained three glucose residues.

Figure 17:
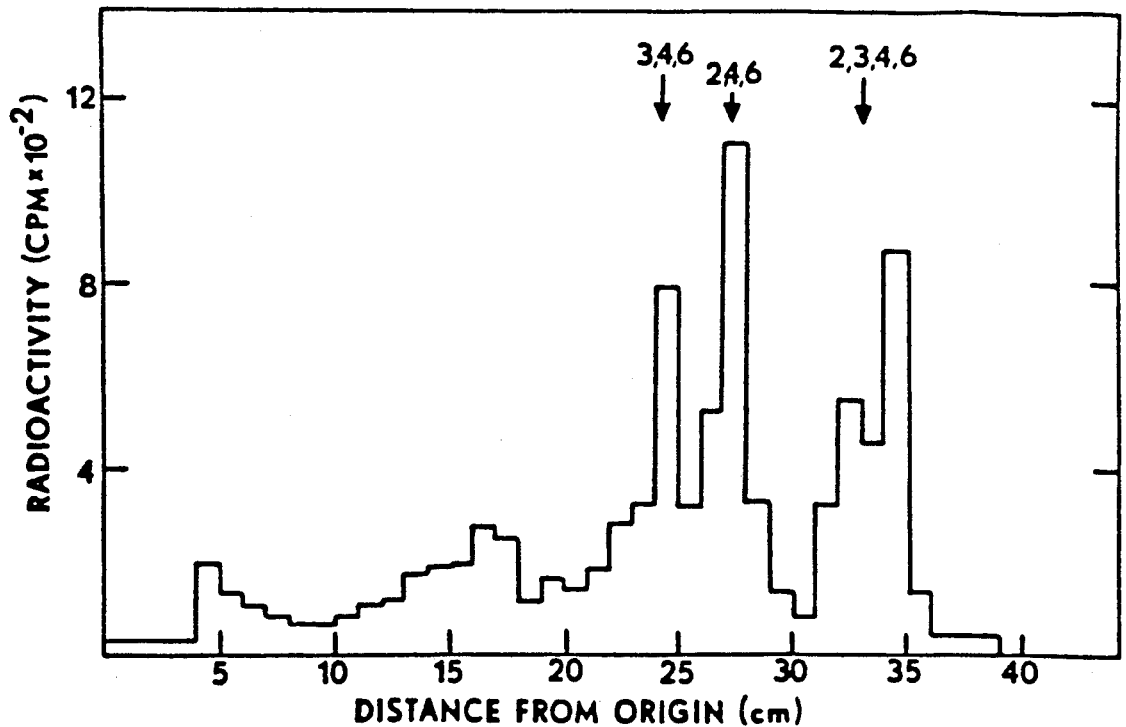
FIG. 17 shows the methylation analysis of the [$^3H$] glucose-labeled oligosaccharide australine-grown virus. The Endo H-released hexose$_{11}$GlcNAc was isolated from the Bio-Gel P-4 column (see FIG. 15) and subjected to complete methylation as described herein. After acid hydrolysis the methylated sugars were analyzed by thin-layer chromatography. Radioactive sugar derivatives were located by scraping plates in 0.5 cm sections followed by liquid scintillation counting. Standard sugars are 3,4,5-trimethylglucose, 2,3,4,6=2,4,6-trimethylglucose, and 2,3,4,6-2,3,4,6-tetramethylglucose.

Further evidence for a Glc$_3$Man$_8$GlcNAc oligosaccharide structure was obtained by methylation analysis of the glucose-labeled, Endo H-released oligosaccharide. For these studies, labeled oligosaccharide produced in the presence of australine was subjected to exhaustive methylation followed by acid hydrolysis, as described under Experimental Procedures. Methylated glucose derivatives were separated by thin-layer chromatography and identified by comparison with methylated glucose standards. The results are shown in FIG. 17. Three major peaks of radioactivity, corresponding to 3,4,6-trimethylglucose, 2,4,6-trimethylglucose and 2,3,4,6-tetramethylglucose, were observed on the thin layer plates. Although the relative proportions of these sugar derivatives did not match the expected 1:1:1 ratio, the identification of three radiolabeled methylated glucose derivatives does indicate the presence of a Glc$_3$-oligosaccharide structure. The deviation from the expected ratio may be due to the fact that australine inhibition of glucosidase I is not complete and therefore small amounts of Glc$_2$Man$_9$GlcNAc or Glc$_1$Man$_9$GlcNAc could also be present in the oligosaccharide fraction used for methylation. Thus, in the in vivo- produced oligosaccharides probably have some inherent heterogeneity.

Effect of Australine on the Formation of Lipid-Linked Saccharides and Protein Synthesis. Since australine appeared to be an inhibitor of glycoprotein processing, it was important to determine whether it inhibited protein synthesis or lipid-linked saccharide formation. For these studies, uninfected MDCK cells were incubated with various amounts of australine and then labeled with either [$^3$H]leucine (for protein) or [$^3$H]mannose (for lipid-linked saccharide). Radioactivity incorporated into protein was determined after TCA precipitation, and radioactivity incorporated into lipid-linked saccharides was determined after organic extraction as detailed above.

Tables I and II show the results of australine treatment on protein synthesis and the formation of lipid-linked saccharides, respectively. It can be seen that australine had little effect on the overall rate of protein synthesis (Table I) at concentrations ranging from 50 to 500 micro g/ml, and for times up to 120 min. Similar results were observed for the incorporation of [$^3$H]mannose into lipid-linked monosaccharides (Table II, left), although the results are somewhat tentative due to the low degree of radiolabel incorporation. In contrast to these observations, however, was the finding that the incorporation of [$^3$H]mannose into lipid-linked oligosaccharide appeared to be stimulated by australine (Table II, right), although the magnitude of the increase was small. At present this phenomenon is incompletely understood, but it may be that australine is inhibiting competing reactions that utilize mannose, thus increasing the amount of mannose available for in vivo glycosylation.

TABLE I

Effect of Australine on the Incorporation of [$^3$H]leucine into Protein$^a$

| Concentration of australine (micro ug/ml) | Radioactivity (cpm) | | Incorporated at Time | |
|---|---|---|---|---|
| | 30 min | 60 min | 90 min | 120 min |
| 0 | 8696 | 15964 | 24404 | 35056 |
| 50 | 9252 | 16572 | 23341 | 33704 |
| 100 | 8304 | 1588 | 25636 | 32008 |
| 250 | 8064 | 13604 | 27776 | 36140 |
| 500 | 9124 | 15648 | 26060 | 32704 |

Uninfected MDCK cells were grown in 6-well Limbro tissue culture dishes. At confluency, australine was added to some wells to the final concentration listed above. After a 2 hours incubation to allow the alkaloid to take effect, [$^3$H]leucine was added to a final concentration of 10 micro Ci/ml, and the incubations were continued. At the times shown, the medium was removed by aspiration, and the monolayers were washed three times with PBS. The cells were released from the wells by scraping, placed in tubes, and extracted with 20% TCA as described above. Radioactivity incorporated into total cellular protein was determined after Pronase digestion by liquid scintillation counting.

TABLE II

Effect of Australine on the Incorporation of [$^3$H]mannose into Lipid-linked Saccharides$^a$

| Concentration of australine (micro g/ml) | Radioactivity (cpm) | | | | | |
|---|---|---|---|---|---|---|
| | Lipid-linked monosaccharides | | | Lipid-linked oligosaccharides | | |
| | 15 min | 30 min | 60 min | 15 min | 30 min | 60 min |
| 0 | 92 | 136 | 160 | 1718 | 4718 | 863 |
| 50 | 97 | 122 | 229 | 1672 | 5021 | 1077 |
| 100 | 101 | 151 | 244 | 2336 | 5335 | 1104 |
| 250 | 107 | 115 | 212 | 2073 | 5661 | 995 |

TABLE II-continued

Effect of Australine on the Incorporation of [$^3$H]mannose into Lipid-linked Saccharides$^a$

| Concentration of australine (micro g/ml) | Radioactivity (cpm) | | | | | |
|---|---|---|---|---|---|---|
| | Lipid-linked monosaccharides | | | Lipid-linked oligosaccharides | | |
| | 15 min | 30 min | 60 min | 15 min | 30 min | 60 min |
| 500 | 96 | 178 | 236 | 2957 | 6167 | 1108 |

$^a$Uninfected MDCK cells were grown in 6-well Limbro tissue culture dishes. At confluency, australine was added to some wells to the final concentrations listed above. After a 2 hour incubation to allow the alkaloid to take effect, [$^3$H]mannose was added to a final concentration of 20 micro Ci/ml, and the incubations were continued. At the times shown, the medium was removed by aspiration, and the monolayers were washed three times with PBS. The cells were released from the wells by scraping, placed in tubes, then sequentially extracted with chloroform:methanol:water (1:1:1) for lipid-linked monosaccharides, and chloroform:methanol:water (10:10:3) for lipid-linked oligosaccharides. The total radioactivity incorporated into the lipid-linked sugars was determined by liquid scintillation counting.

Figure 14:
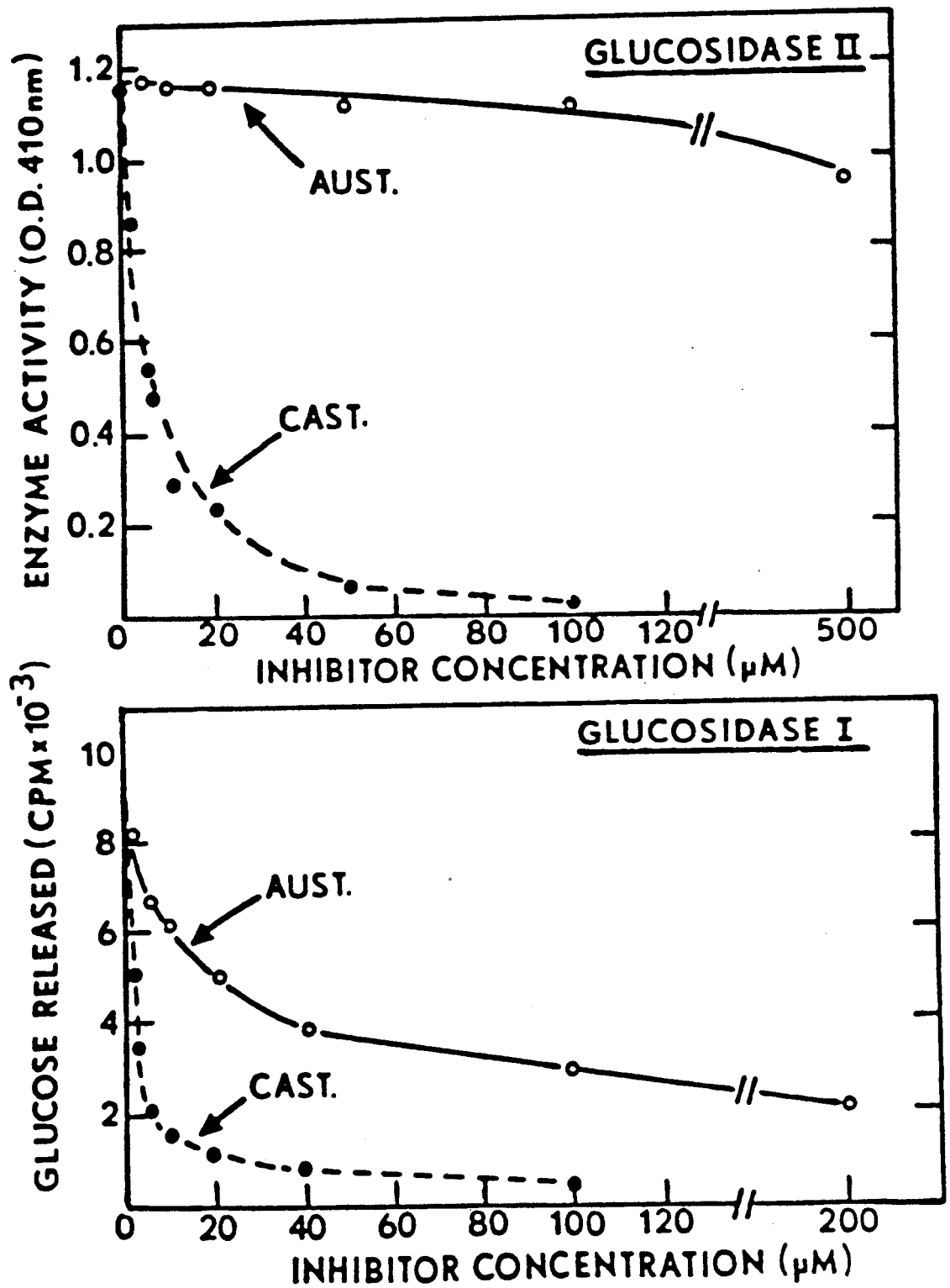
FIG. 14 shows the effect of australine and castanospermine on the activity of the mung bean processing enzymes, glucosidase I and glucosidase II. Conditions were as described herein. Glucosidase II activity was determined by monitoring the release of p-nitrophenol from p-nitrophenyl-alpha-D-glucoside (upper panel). Glucosidase I activity was determined by measuring the release of [$^3H$] glucose from glucose-labeled $Glc_3Man_9GlcNAc$ oligosaccharide (lower panel). Australine (AUST), . Castanospermine (CAST), .

Studies described herein demonstrate that the pyrrolizidine alkaloid, australine, is a specific competitive inhibitor of amyloglucosidase, an alpha-1 → 4, alpha-1 → 6 exoglucosidase (see FIGS. 10 and 11), but does not inhibit beta-glucosidase or any other alpha- or beta-glycosidases tested. In addition, australine was a reasonably good inhibitor of glucosidase I, but was a very poor inhibitor of glucosidase II (FIG. 14). Thus, this alkaloid appears to be the first glucosidase inhibitor that is active towards glucosidase I without also affecting glucosidase II.

Since australine inhibited glucosidase I activity in vitro, it was tested in cell culture as a potential inhibitor of glycoprotein processing. For these studies the influenza virus-infected MDCK cell culture system was employed. The results clearly demonstrated that australine altered the normal glycoprotein processing of viral glycoproteins (FIG. 15), but did not do so by an inhibition of protein synthesis (Table I) or lipid-linked oligosaccharide (or monosaccharide) formation (Table II). The major oligosaccharide produced in the presence of australine and released by Endo H appeared to be a Glc$_3$Man$_8$GlcNAc structure, based on chromatographic (FIG. 16), enzymatic (FIG. 16) and text), and chemical (FIG. 17) analyses. Thus, these data were consistent with the observed inhibition of glucosidase I by australine, in vitro. However, relative to other processing inhibitors, a fairly high concentration of australine was required to produce marked effects on glycoprotein processing. For example, castanospermine, a glucosidase I and glucosidase II inhibitor, at a concentration of 10 micro g/ml, produced the same degree of inhibition (e.g., an increased proportion of Endo H-susceptible glycopeptides) that was observed for 500 micro g/ml australine, in vivo (5).

Australine is, however, the first pyrrolizidine alkaloid that has been shown to have biological activity and to be a glycosidase inhibitor. From a structure-activity point of view, it would appear that the six-membered ring structure, which is characteristic of the indolizidine alkaloids (castanospermine, 6-epicastanospermine and swainsonine; (62, 18) as well as other related inhibitors (deoxynojirimycin and deoxymannojirimycin (63, 64) is not necessary for a compound to be an inhibitor of glycosidases. Thus, the ring nitrogen and the configuration of the hydroxyl groups relative to this nitrogen may be the only factors required for such an inhibitor. In this regard, it is interesting to point out that several previous studies showed that the furanose derivatives, 1,4-dideoxy4-imino-D-mannitol and 2,5-dihydroxymethyl-3,4-dihydroxypyrrolidine, were inhibitors of mannosidase I and glucosidase I, respectively (65, 66). Nevertheless, australine with its unique tetrahydroxylated pyrrolizidine structure does add to the growing list of chemical structures that can have important biological activity.

Citations in the following list are incorporated by reference herein for the reasons cited:

REFERENCES

1. S. L. Everist, "Poisonous Plants of Australia," 2nd ed., Angus & Robertson, Sydney, Australia, 1981, pp. 403-405.
2. L. D. Hohenschutz, E. A. Bell, P. J. Jewess, D. P. Leworthy, R. J. Pryce, E. Arnold, and J. Clardy, *Phytochemistry*, 20, 811 (1981).
3. R. Saul, J. P. Chambers, R. J. Molyneux, and A. D. Elbein, *Arch. Biochem. Biophys.*, 221, 593 (1983).
4. R. Saul, R. J. Molyneaux, and A. D. Elbein, *Arch. Biochem. Biophys.* 230, 668 (1984).
5. Y. T. Pan, H. Hori, R. Saul, B. A. Sandord, R. J. Molyneux, and A. D. Elbein, *Biochemistry*, 22, 3975 (1983).
6. D. L. Dreyer, K. C. Jones, and R. J. Molyneux, *J. Chem. Ecol.* 11, 1045 (1985).
7. R. J. Nash, K. A. Fenton, A. M. R. Gatehouse, and E. A. Bell, *Entomol. exp. appl.* 42, 71 (1986).
8. K. L. Stevens and R. J. Molyneux, *J. Chem. Ecol.* 14, 1467 (1988).
9. R. Saul., J. J. Ghidoni, R. J. Molyneux, and A. D. Elbein, *Proc. Natl. Acad. Sci.* 82, 93 (1985).
10. B. L. Rhinehart, K. M. Robinson, A. J. Payne, M. E. Wheatley, J. L. Fisher, P. S. Liu, and W. Cheng, *Life Sci.* 41, 2325 (1987).
11. B. D. Walker, M. Kowalski, W. C. Rosen, L. R. Rohrschneider, W. A. Haseltine, and J. Sodroski, *Proc. Natl. Acad. Sci.* 84, 8120 (1987).
12. P. S. Sunkara, T. L. Bowlin, P. S. Liu, and A. Sjoerdsma, *Biochem. Biophys. Res. Commun.* 148, 206 (1987).
13. G. K. Ostrander, N. K. Scribner, and L. R. Rohrschneider, *Cancer Res.* 48, 1091 (1988).
14. R. J. Molyneux and L. F. James, *Science*, 216, 190 (1982).
15. S. M. Colegate, P. R. Dorling, and C. R. Huxtable, *Aust. J. Chem.* 32, 2257 (1979).
16. M. J. Humphries, K. Matsumoto, S. L. White, R. J. Molyneux, and K. Olden, *Cancer Res.* 48, 1410 (1988).
17. A. D. Elbein and R. J. Molyneux, in: "*Alkaloids: Chemical and Biological Perspectives,*" Ed. by S. W. Pelletier, Wiley, New York, 1987, Vol. 5, pp. 1-54.
18. Kornfeld, R. & Kornfeld, S. (1976) *Annu. Rev. Biochem.* 45, 217-327.
19. Wagh, P. V. & Bahl, D. P. (1981) *CRC Crit. Rev. Biochem.* 10, 307-377.
20. Elbein, A. D. (1979) *Annu. Rev. Plant Physiol.* 30, 239-272.
21. Struck, D. K. & Lennarz, W. J. (1980) in The Biochemistry of Glycoproteins and Proteoglycans (Lennarz, W., Ed.), pp. 35-83, Plenum Press,
22. Kornfeld, R. & Kornfeld, S. (1985) *Annu. Rev. Biochem.* 54, 631-664.
23. Turco, S. J. & Robbins, P. W. (1976) *J. Biol. Chem.* 254, 4560-4567.
24. Grinna, L. S. & Robbins, P. W. (1979) *J. Biol. Chem.* 254, 8814-8818.
25. Hubbard, S. C. & Ivatt, R. J. (1981) *Annu. Rev. Biochem.* 50, 553-583.

26. Elting, J. J., Chen, W. W., & Lennarz, W. J. (1980) *J. Biol. Chem.* 255, 2325-2331.
27. Chen, W. W. & Lennarz, W. J. (1978) *J. Biol. Chem.* 253, 5780-5785.
28. Grinna, L. S. & Robbins, P. W. (1979) *J. Biol. Chem.* 254, 8814-8818.
29. Grinna, L. S. & Robbins, P. W. (1980) *J. Biol. Chem.* 255, 2255-2258.
30. Ugalda, R. A., Staneloni, R. J., & Leloir, L. F. (1978) *FEBS Lett.* 91, 209-212.
31. Kilker, R. D., Jr., Saunier, B., Tkacz, J. S., & Herscovics, A. (1981) *J. Biol. Chem.* 256, 5299-5303.
32. Bischoff, J. & Kornfeld, R. (1983) *J. Biol. Chem.* 288, 7970-7910.
33. Bischoff, J., Liscum, L., & Kornfeld, R. (1986) *J. Biol. Chem.* 261, 4766-4774.
34. Kornfeld, S., Le, E., & Tabas, I, (1978) *J. Biol. Chem.* 253, 7770-7778.
35. Opheim, D. J. & Touster, O. (1978) *J. Biol. Chem.* 253, 1017-1023.
36. Tabas, I. & Kornfeld, S. (1979) *J. Biol. Chem.* 254, 11655-11663.
37. Forsee, W. T. & Schutzback, J. (1981) *J. Biol. Chem.* 256, 6577-6583.
38. Tulsiani, D. R. P., Hubbard, S. C., Robbins, P. W., & Touster, O. (1982a) *J. Biol. Chem.* 257, 3660-3668.
39. Tabas, I. & Kornfeld, S. (1978) *J. Biol. Chem.* 253, 7779-7786.
40. Harpaz, N. & Schachter, H. (1980a) *J. Biol. Chem.* 255, 4885-5893.
41. Narasimhan, S., Stanley, P., & Schachter, H. (1977) *J. Biol. Chem.* 252, 3926-3933.
42. Harpaz, N. & Schachter, H. (1980b) *J. Biol. Chem.* 255, 4894-4902.
43. Tulsiani, D. R. P. & Touster, O. (1983) *J. Biol. Chem.* 258, 7578-7585.
44. Schachter, H. & Roseman, S. (1980) in The Biochemistry of Glycoproteins and Proteoglycans (Lennarz, W., Ed.), pp. 85-160, Plenum Press, New York.
45. Schwarz, R. T. & Datema, R. (1982) *Adv. Carbohydr. Chem. Biochem.* 40, 287-379.
46. Elbein, A. D., Solf, R., Dorling, P. R., & Vosbeck, K. (1981) *Proc. Natl. Acad. Sci. USA* 78, 7393-7397.
47. Tulsiani, D. R. P., Harris, T. M., & Touster, O. (1982b) *J. Biol. Chem.* 257, 7936-7939.
48. Legler, G. & Julich, E. (1984) *Carbohydr. Res.* 128, 61-72.
49. Fuhrmann, U., Bause, E., Legler, G., & Ploegh, H. (1984) *Nature* 307, 755-758.
50. Szumilo, T., Kaushal, G. P., & Elbein, A. D. (1986) *Arch. Biochem. Biophys.* 247, 261-271.
51. Elbein, A. D., Ayda, S., & Lee, Y. C. (1977) *J. Biol. Chem.* 252, 2206-2211.
52. Szumilo, T. & Elbein, A. D. (1985) *Anal. Biochem.* 151, 32-40.
53. Molyneux, R. J., Benson, M., Wong, R. Y., Tropea, J. T., & Elbein, A. D. (1988) *J. Natural Products, In Press.*
54. Molyneux, R. J., Roitman, J. N., Dunnheim, G., Szumilo, T., & Elbein, A. D. (1986) *Arch. Biochem. Biophys.* 251, 450-457.
55. Rudick, M. & Elbein, A. D. (1973) *J. Biol. Chem.* 248, 6506-6512.
56. Nelson, N. (1944) *J. Biol. Chem.* 153, 375-380.
57. Elbein, A. D., Vosbeck, K., Dorlin, P. R., & Horisberger, M. (1982) *J. Biol. Chem.* 257, 1573-1576.
58. Sanford, P. A. & Conrad, H. (1966) *Biochemistry* 5, 1508-1517.
59. Hakomori, S. (1964) *J. Biochem.* (Tokyo) 55, 205-208.
60. Chambers, J. & Elbein, A. D. (1975) *J. Biol. Chem.* 250, 6904-6913.
61. Trugnan, G., Rousett, M., & Zweibaum, A. (1986) *FEBS Lett.* 195, 28-32.
62. Elbein, A. D. (1987) *Annu. Rev. Biochem.* 56, 497-534.
63. Saunier, B., Kilker, R. P., Tkacz, J. S., Quaroni, A., & Herscovics, A. (1982) *J. Biol. Chem.* 257, 14155-14162.
64. Elbein, A. D., Legler, G., Tlusty, A., McDowell, W., & Schwarz, R. T. (1984a) *Arch. Biochem. Biophys.* 235, 579-588.
65. Palamarczyk, G., Mitchell, M., Smith, P. W., Fleet, G. W. J., & Elbein, A. D. (1985) *Arch. Biochem. Biophys.* 243, 35-45.
66. Elbein, A. D., Mitchell, M., Sanford, B. A., Fellows, L. E., & Evans, S. V. (1984b) *J. Biol. Chem.* 259, 12409-12413.
67. R. J. Molyneux, J. N. Roitman, G. Dunnheim, J.T. Szumilo, and A. D. Elbein, *Arch. Biochem. Biophys.* 251, 450 (1987).
68. M. Koyama and S. Sakamura, *Agr. Biol. Chem.* 38, 1111 (1974).
69. S. V. Evans, A. R. Hayman, L. E. Fellows, T. K. M. Shing, A. E. Derome, and G. W. J. Fleet, *Tetrahedron Lett.* 26, 1465 (1985).
70. R. J. Molyneux, L. F. James, and K. E. Panter, in: "Plant Toxicology," Ed. by A. A. Seawright, M. P. Hegarty, L. F. James, and R. F. Keeler, *Queensland Poisonous Plants Comm.*, Brisbane, Australia, 1985, pp. 266-278.
71. L. B. Bull, C. C. J. Culvenor, and A. T. Dick, "The Pyrrolizidine Alkaloids: Their Chemistry, Pathogenicity and Other Biological Properties," North-Holland, Amsterdam, 1968, pp. 40-54.
72. R. S. Sawhney, C. K. Atal, C. C. J. Culvenor and L. W. Smith, *Aust. J. Chem.* 27, 1805 (1974).

Changes may be made in the chemical substitutions and functional groups described herein or in the steps or the sequence of steps of the methods described herein without departing from the concept and scope of the inventions as defined in the following claims.

What is claimed is:

1. A purified bioactive compound having the formula:

$$\begin{array}{c} R_1O \quad H \quad OR_2 \\ \text{(pyrrolizidine ring with positions 7, 7a, 1, 6, 5, N, 3, 2)} \\ \text{—}OR_3 \\ CH_2OR_4 \end{array}$$

wherein at least one of $R_1$, $R_2$, $R_3$ and $R_4$ is H or acyl having less than about five carbon atoms.

2. The purified bioactive compound of claim 1 wherein $R_1$, $R_2$, $R_3$ and $R_4$ are H.

3. The purified bioactive compound of claim 1 wherein $R_1$, $R_2$, $R_3$ and $R_4$ are acetyl.

4. Purified (1R, 2R, 3R, 7S, 7aR)-3-hydroxymethyl-1,2,7-trihydroxypyrrolizidine.

5. A method of interfering with glycoprotein processing in influenza-infected cells, comprising adding an amount of australine to the cells, the amount being sufficient to inhibit glycoprotein processing in influenza-infected cells.

6. The method of claim 5 wherein the australine is (1R, 2R, 3R, 7S, 7aR)-3-hydroxymethyl-1,2,7-trihydroxypyrrolizidine.

7. The method of claim 5 wherein the bioactive compound is australine having the formula:

[structure]

wherein at least one of $R_1$, $R_2$, $R_3$ and $R_4$ are H or acyl having less than about five carbon atoms.

8. The method of claim 5 wherein the bioactive compound is australine having the formula:

[structure]

wherein each of $R_1$, $R_2$, $R_3$ and $R_4$ are acetyl.

9. The method of claim 5 wherein the amount of australine sufficient to inhibit glycoprotein processing in influenza-infected cells is about 500 µg/ml.

* * * * *